United States Patent [19]
Thompson et al.

[11] Patent Number: 5,703,219
[45] Date of Patent: Dec. 30, 1997

[54] **NUCLEIC ACID ENCODING *HELICOBACTER PYLORI* ENOLASE**

[75] Inventors: Stuart A. Thompson, Joelton; Martin J. Blaser, Nashville, both of Tenn.

[73] Assignee: Vanderbilt University, Nashville, Tenn.

[21] Appl. No.: 446,920

[22] Filed: May 22, 1995

Related U.S. Application Data

[63] Continuation-in-part of Ser. No. 215,928, Mar. 21, 1994, Pat. No. 5,434,253.

[51] Int. Cl.$^6$ .......................... C07H 21/04; C12N 15/63; C12N 1/21
[52] U.S. Cl. .................. 536/23.2; 435/320.1; 435/252.3
[58] Field of Search .............. 536/23.2; 435/320.1, 435/252.3

[56] References Cited

PUBLICATIONS

Story et al. *Science* 259:1892–1896, Mar. 26, 1993.
Roca and Cox *Crit. Rev. Biochem. Mol. Biol.* 25(6):415–56, 1990.
Labigne–Roussel et al. *J. Bacteriol.* 170(4):1704–1708, Apr. 1988.
Perez–Perez and Blaser *Infect. Immun.* 55(5):1256–1263, May 1987.
Keener et al. *J. Bact* 160(1):153–160, Oct. 1984.
Leyva–Vazquez, M.A. et al. (1994) "Cloning and nucleotide sequences of the genes encoding thriose phosphate isomerase, phosphoglycerate mutase, and enolase from Bacillus subtilis" *J. Bact.* 176(13):3903–3910, Jul. 1994.
Burnett, M.E. et al. (1992) "Molecular characterization of the Zymomonas mobilis enoase (eno) gene" *J. Bact.* 174(20):6548–6553, Oct. 1992.

*Primary Examiner*—Robert A. Wax
*Assistant Examiner*—Kawai Lau
*Attorney, Agent, or Firm*—Needle & Rosenberg, PC

[57] ABSTRACT

An isolated nucleic acid encoding the *Helicobacter pylori* recombinase is provided. Also provided is an isolated nucleic acid that hybridizes with the recombinase-encoding nucleic acid under stringent conditions and has at least 70% complementarity with the segment of the nucleic acid of SEQ ID NO:1 to which it hybridizes. Also provided is a mutant strain of *H. pylori* that does not express a functional recombinase (recA$^-$ mutant). An isolated nucleic acid encoding the *Helicobacter pylori* enolase is provided. Also provided is an isolated nucleic acid that hybridizes with the nucleic acid that encodes a *H. pylori* recombinase under stringent conditions and has at least 70% complementarity with the segment of the nucleic acid of SEQ ID NO:9 to which it hybridizes. Also provided is a mutant strain of *H. pylori* that does not express a functional enolase (eno$^-$ mutant). A method is provided for immunizing a subject against infection by *H. pylori* by administering to the subject an immunogenic amount of mutant *H. pylori* in a carrier for the mutant.

8 Claims, 6 Drawing Sheets

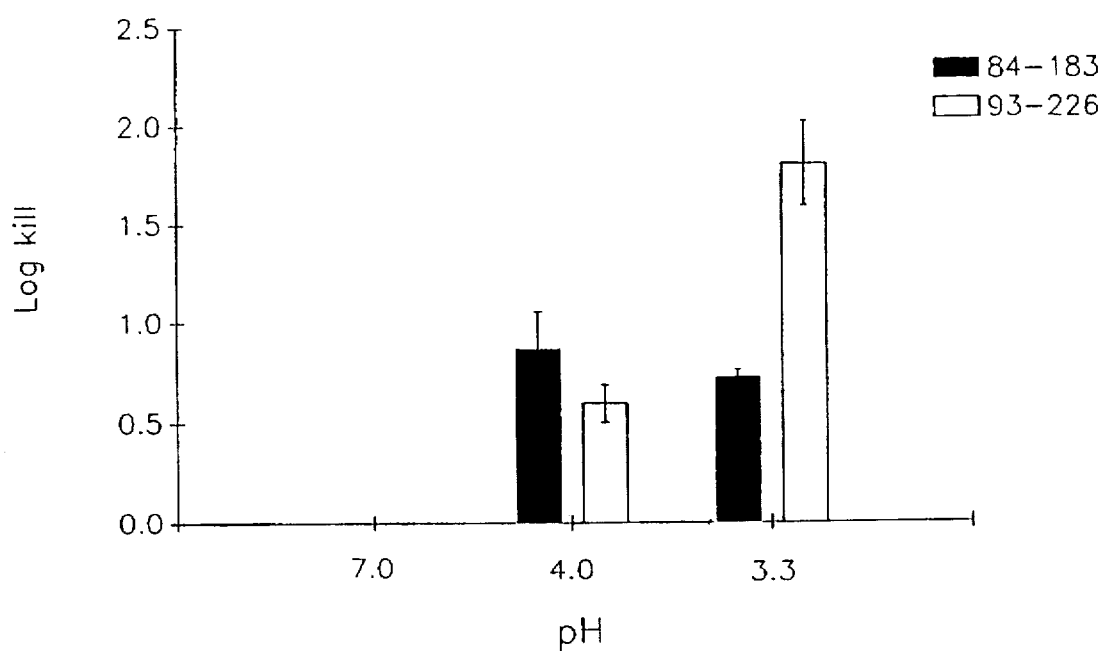

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 1169 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 349..1167

( x i ) SEQUENCE DESCRIPTION: SEQ ID NO:1:

```
TTTTTTCACT  AATTTAGCCA  TAGCCATTCC  CAAAGCGGGA  GTAGTAATCG  TTCGCAATTT      60

TAGGGTATAG  CCCAAAGCTG  ATCGCGCTCA  CATCATAAGT  GTTTTTAGG   GCTTCTTGGT     120

TTAGGGTTTC  AATATCCAGG  GCAATGTTGT  GGAATGTTTT  ATTTTAATG   GGGCAATCTA     180

TCCAGCCAAA  CTTAATCGCA  TAATACATGA  AAATATCATC  AGCATCAGGG  CTATGAGCGA     240

CACTAATCAA  AGTAAAATCC  TTTTGTGATA  GGGTAAGTCC  TTTTATTATA  ATAGATTTTA     300

GGCTAGGATT  TGATAGAATA  AACAAATCAA  ATTCAATAAG  GTGATTTA ATG GCA ATA       357
                                                         Met Ala Ile
                                                           1

GAT GAA GAC AAA CAA AAA GCG ATT TCT TTA GCG ATC AAA CAA ATT GAT          405
Asp Glu Asp Lys Gln Lys Ala Ile Ser Leu Ala Ile Lys Gln Ile Asp
```

-continued

|     | 5   |     |     |     | 10  |     |     |     |     | 15  |     |     |     |     |      |
|-----|-----|-----|-----|-----|-----|-----|-----|-----|-----|-----|-----|-----|-----|-----|------|
| AAG | GTT | TTT | GGT | AAG | GGG | GCG | TTG | GTA | CGC | CTT | GGG | GAT | AAG | CAA | GTA | 453 |
| Lys | Val | Phe | Gly | Lys | Gly | Ala | Leu | Val | Arg | Leu | Gly | Asp | Lys | Gln | Val |     |
|  20 |     |     |     |  25 |     |     |     |     |  30 |     |     |     |     |  35 |     |

| GAA | AAG | ATT | GAC | GCT | ATT | TCT | ACA | GGC | TCG | TTA | GGA | TTG | GAT | TTA | GCT | 501 |
| Glu | Lys | Ile | Asp | Ala | Ile | Ser | Thr | Gly | Ser | Leu | Gly | Leu | Asp | Leu | Ala |     |
|     |     |     |     |  40 |     |     |     |     |  45 |     |     |     |     |  50 |     |

| TTA | GGG | ATT | GGG | GGC | GTT | CCA | AAG | GGT | AGG | ATC | ATT | GAA | ATT | TAT | GGG | 549 |
| Leu | Gly | Ile | Gly | Gly | Val | Pro | Lys | Gly | Arg | Ile | Ile | Glu | Ile | Tyr | Gly |     |
|     |     |     |     |  55 |     |     |     |     |  60 |     |     |     |     |  65 |     |

| CCA | GAG | TCA | AGC | GGG | AAG | ACC | ACT | CTA | AGC | TTG | CAT | ATT | ATT | GCA | GAA | 597 |
| Pro | Glu | Ser | Ser | Gly | Lys | Thr | Thr | Leu | Ser | Leu | His | Ile | Ile | Ala | Glu |     |
|     |     |  70 |     |     |     |     |  75 |     |     |     |     |  80 |     |     |     |

| TGC | CAA | AAA | AAT | GGC | GGC | GTG | TGC | GCG | TTC | ATT | GAC | GCT | GAA | CAT | GCC | 645 |
| Cys | Gln | Lys | Asn | Gly | Gly | Val | Cys | Ala | Phe | Ile | Asp | Ala | Glu | His | Ala |     |
|     |  85 |     |     |     |     |  90 |     |     |     |     |  95 |     |     |     |     |

| TTA | GAT | GTG | TAT | TAT | GCC | AAG | AGG | CTA | GGC | GTG | GAT | ACA | GAA | AAT | CTA | 693 |
| Leu | Asp | Val | Tyr | Tyr | Ala | Lys | Arg | Leu | Gly | Val | Asp | Thr | Glu | Asn | Leu |     |
| 100 |     |     |     |     | 105 |     |     |     |     | 110 |     |     |     |     | 115 |

| CTC | GTT | TCC | CAA | CCA | AGC | ACG | GGC | GAA | GAA | GCC | TTA | GAA | ATT | TTA | GAA | 741 |
| Leu | Val | Ser | Gln | Pro | Ser | Thr | Gly | Glu | Glu | Ala | Leu | Glu | Ile | Leu | Glu |     |
|     |     |     |     | 120 |     |     |     |     | 125 |     |     |     |     | 130 |     |

| ACG | ATC | ACC | AGA | AGC | GGA | GGG | ATT | GAT | TTA | GTG | GTG | GTG | GAT | TCG | GTG | 789 |
| Thr | Ile | Thr | Arg | Ser | Gly | Gly | Ile | Asp | Leu | Val | Val | Val | Asp | Ser | Val |     |
|     |     |     | 135 |     |     |     |     | 140 |     |     |     |     | 145 |     |     |

| GCG | GCC | CTT | ACG | CCT | AAA | GCG | GAG | ATT | GAT | GGG | GAT | ATG | GGC | GAT | CAG | 837 |
| Ala | Ala | Leu | Thr | Pro | Lys | Ala | Glu | Ile | Asp | Gly | Asp | Met | Gly | Asp | Gln |     |
|     |     | 150 |     |     |     |     | 155 |     |     |     |     | 160 |     |     |     |

| CAT | GTG | GGC | TTG | CAA | GCA | AGG | CTT | ATG | AGC | CAT | GCG | TTA | AGA | AAA | ATC | 885 |
| His | Val | Gly | Leu | Gln | Ala | Arg | Leu | Met | Ser | His | Ala | Leu | Arg | Lys | Ile |     |
|     | 165 |     |     |     |     | 170 |     |     |     |     | 175 |     |     |     |     |

| ACT | GGT | GTC | TTG | CAC | AAG | ATG | AAC | ACC | ACT | CTC | ATT | TTT | ATC | AAT | CAA | 933 |
| Thr | Gly | Val | Leu | His | Lys | Met | Asn | Thr | Thr | Leu | Ile | Phe | Ile | Asn | Gln |     |
| 180 |     |     |     |     | 185 |     |     |     |     | 190 |     |     |     |     | 195 |

| ATA | AGG | ATG | AAG | ATC | GGC | ATG | ACA | GGT | TAT | GGG | AGT | CCA | GAG | ACC | ACA | 981 |
| Ile | Arg | Met | Lys | Ile | Gly | Met | Thr | Gly | Tyr | Gly | Ser | Pro | Glu | Thr | Thr |     |
|     |     |     |     | 200 |     |     |     |     | 205 |     |     |     |     | 210 |     |

| ACC | GGA | GGC | AAT | GCC | TTA | AAA | TTC | TAT | GCG | AGC | GTT | AGG | ATT | GAT | ATT | 1029 |
| Thr | Gly | Gly | Asn | Ala | Leu | Lys | Phe | Tyr | Ala | Ser | Val | Arg | Ile | Asp | Ile |      |
|     |     |     | 215 |     |     |     |     | 220 |     |     |     |     | 225 |     |     |

| AGA | AGA | ATC | GCC | GCT | TTA | AAA | CAA | AAC | GAA | CAG | CAT | ATC | GGT | AAT | AGG | 1077 |
| Arg | Arg | Ile | Ala | Ala | Leu | Lys | Gln | Asn | Glu | Gln | His | Ile | Gly | Asn | Arg |      |
|     |     |     | 230 |     |     |     |     | 235 |     |     |     |     | 240 |     |     |

| GCT | AAA | GCT | AAA | GTC | GTT | AAA | AAT | AAA | GTC | GCT | CCG | CCC | TTT | AGA | GAA | 1125 |
| Ala | Lys | Ala | Lys | Val | Val | Lys | Asn | Lys | Val | Ala | Pro | Pro | Phe | Arg | Glu |      |
|     | 245 |     |     |     |     | 250 |     |     |     |     | 255 |     |     |     |     |

| GCG | GAA | TTT | GAC | ATC | ATG | TTT | GGG | GAA | GGG | ATT | TCT | AAA | GAG |     |     | 1167 |
| Ala | Glu | Phe | Asp | Ile | Met | Phe | Gly | Glu | Gly | Ile | Ser | Lys | Glu |     |     |      |
| 260 |     |     |     |     | 265 |     |     |     |     | 270 |     |     |     |     |     |

| GG  |     |     |     |     |     |     |     |     |     |     |     |     |     |     |     | 1169 |

( 2 ) INFORMATION FOR SEQ ID NO:2:

( i ) SEQUENCE CHARACTERISTICS:
        ( A ) LENGTH: 273 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

-continued

```
Met Ala Ile Asp Glu Asp Lys Gln Lys Ala Ile Ser Leu Ala Ile Lys
 1               5                  10                  15

Gln Ile Asp Lys Val Phe Gly Lys Gly Ala Leu Val Arg Leu Gly Asp
                20                  25                  30

Lys Gln Val Glu Lys Ile Asp Ala Ile Ser Thr Gly Ser Leu Gly Leu
            35                  40                  45

Asp Leu Ala Leu Gly Ile Gly Gly Val Pro Lys Gly Arg Ile Ile Glu
        50                  55                  60

Ile Tyr Gly Pro Glu Ser Ser Gly Lys Thr Thr Leu Ser Leu His Ile
65                  70                  75                  80

Ile Ala Glu Cys Gln Lys Asn Gly Gly Val Cys Ala Phe Ile Asp Ala
                85                  90                  95

Glu His Ala Leu Asp Val Tyr Tyr Ala Lys Arg Leu Gly Val Asp Thr
            100                 105                 110

Glu Asn Leu Leu Val Ser Gln Pro Ser Thr Gly Glu Glu Ala Leu Glu
        115                 120                 125

Ile Leu Glu Thr Ile Thr Arg Ser Gly Gly Ile Asp Leu Val Val Val
        130                 135                 140

Asp Ser Val Ala Ala Leu Thr Pro Lys Ala Glu Ile Asp Gly Asp Met
145                 150                 155                 160

Gly Asp Gln His Val Gly Leu Gln Ala Arg Leu Met Ser His Ala Leu
                165                 170                 175

Arg Lys Ile Thr Gly Val Leu His Lys Met Asn Thr Thr Leu Ile Phe
            180                 185                 190

Ile Asn Gln Ile Arg Met Lys Ile Gly Met Thr Gly Tyr Gly Ser Pro
        195                 200                 205

Glu Thr Thr Thr Gly Gly Asn Ala Leu Lys Phe Tyr Ala Ser Val Arg
210                 215                 220

Ile Asp Ile Arg Arg Ile Ala Ala Leu Lys Gln Asn Glu Gln His Ile
225                 230                 235                 240

Gly Asn Arg Ala Lys Ala Lys Val Val Lys Asn Lys Val Ala Pro Pro
                245                 250                 255

Phe Arg Glu Ala Glu Phe Asp Ile Met Phe Gly Glu Gly Ile Ser Lys
            260                 265                 270

Glu
```

( 2 ) INFORMATION FOR SEQ ID NO:3:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION:
    ( D ) OTHER INFORMATION: /label=X
      / note="X =Y OR F"

( x i ) SEQUENCE DESCRIPTION: SEQ ID NO:3:

```
Glu Ile Xaa Gly Pro Glu
 1               5
```

( 2 ) INFORMATION FOR SEQ ID NO:4:

( i ) SEQUENCE CHARACTERISTICS:
    ( A ) LENGTH: 17 base pairs (B) TYPE: nucleic acid
                    (C) STRANDEDNESS: single
                    (D) TOPOLOGY: linear (ii) MOLECULE TYPE: oligonucleotide (xi) SEQUENCE DESCRIPTION: SEQ ID NO:4:

GARATHTWYGG NCCNGA                                                                    17

(2) INFORMATION FOR SEQ ID NO:5:

(i) SEQUENCE CHARACTERISTICS:
                    (A) LENGTH: 7 amino acids
                    (B) TYPE: amino acid
                    (C) STRANDEDNESS: single
                    (D) TOPOLOGY: linear (ii) MOLECULE TYPE: peptide (xi) SEQUENCE DESCRIPTION: SEQ ID NO:5:

Asn  Ala  Leu  Lys  Phe  Tyr  Ala
      1               5

(2) INFORMATION FOR SEQ ID NO:6:

(i) SEQUENCE CHARACTERISTICS:
                    (A) LENGTH: 17 base pairs
                    (B) TYPE: nucleic acid
                    (C) STRANDEDNESS: single
                    (D) TOPOLOGY: linear (ii) MOLECULE TYPE: oligonucleotide (xi) SEQUENCE DESCRIPTION: SEQ ID NO:6:

GCRTARAAYT TNARNGC                                                                    17

(2) INFORMATION FOR SEQ ID NO:7:

(i) SEQUENCE CHARACTERISTICS:
                    (A) LENGTH: 18 base pairs
                    (B) TYPE: nucleic acid
                    (C) STRANDEDNESS: single
                    (D) TOPOLOGY: linear (ii) MOLECULE TYPE: oligonucleotide (xi) SEQUENCE DESCRIPTION: SEQ ID NO:7:

GTGAAAGCGA AAAACAAG                                                                   18

(2) INFORMATION FOR SEQ ID NO:8:

(i) SEQUENCE CHARACTERISTICS:
                    (A) LENGTH: 21 base pairs
                    (B) TYPE: nucleic acid
                    (C) STRANDEDNESS: single
                    (D) TOPOLOGY: linear (ii) MOLECULE TYPE: oligonucleotide (xi) SEQUENCE DESCRIPTION: SEQ ID NO:8:

AAGAGAAGCT TTAAACCCTC C                                                               21

(2) INFORMATION FOR SEQ ID NO:9:

(i) SEQUENCE CHARACTERISTICS:
                    (A) LENGTH: 1937 base pairs
                    (B) TYPE: nucleic acid
                    (C) STRANDEDNESS: double
                    (D) TOPOLOGY: linear (ii) MOLECULE TYPE: DNA (genomic)

(ix) FEATURE:
    (A) NAME/KEY: CDS
    (B) LOCATION: 350..1393

(ix) FEATURE:
    (A) NAME/KEY: CDS
    (B) LOCATION: 1405..1937

(xi) SEQUENCE DESCRIPTION: SEQ ID NO:9:

```
TTTTTTTCAC TAATTTAGCC ATAGCCATTC CCAAAGCGGG AGTAGTAATC GTTCGCAATT      60

TTAGGGTATA GCCCAAAGCT GATCGCGCTC ACATCATAAG TGTTTTTTAG GGCTTCTTGG     120

TTTAGGGTTT CAATATCCAG GGCAATGTTG TGGAATGTTT TATTTTAAT GGGGCAATCT     180

ATCCAGCCAA ACTTAATCGC ATAATACATG AAAATATCAT CAGCATCAGG GCTATGAGCG     240

ACACTAATCA AAGTAAAATC CTTTGTGAT AGGGTAAGTC CTTTATTAT AATAGATTTT     300

AGGCTAGGAT TTGATAGAAT AAACAAATCA AATTCAATAA GGTGATTTA ATG GCA        355
                                                      Met Ala
                                                       1

ATA GAT GAA GAC AAA CAA AAA GCG ATT TCT TTA GCG ATC AAA CAA ATT      403
Ile Asp Glu Asp Lys Gln Lys Ala Ile Ser Leu Ala Ile Lys Gln Ile
         5                  10                  15

GAT AAG GTT TTT GGT AAG GGG GCG TTG GTA CGC CTT GGG GAT AAG CAA      451
Asp Lys Val Phe Gly Lys Gly Ala Leu Val Arg Leu Gly Asp Lys Gln
     20                  25                  30

GTA GAA AAG ATT GAC GCT ATT TCT ACA GGC TCG TTA GGA TTG GAT TTA      499
Val Glu Lys Ile Asp Ala Ile Ser Thr Gly Ser Leu Gly Leu Asp Leu
 35                  40                  45                  50

GCT TTA GGG ATT GGG GGC GTT CCA AAG GGT AGG ATC ATT GAA ATT TAT      547
Ala Leu Gly Ile Gly Gly Val Pro Lys Gly Arg Ile Ile Glu Ile Tyr
             55                  60                  65

GGG CCA GAG TCA AGC GGG AAG ACC ACT CTA AGC TTG CAT ATT ATT GCA      595
Gly Pro Glu Ser Ser Gly Lys Thr Thr Leu Ser Leu His Ile Ile Ala
         70                  75                  80

GAA TGC CAA AAA AAT GGC GGC GTG TGC GCG TTC ATT GAC GCT GAA CAT      643
Glu Cys Gln Lys Asn Gly Gly Val Cys Ala Phe Ile Asp Ala Glu His
     85                  90                  95

GCC TTA GAT GTG TAT TAT GCC AAG AGG CTA GGC GTG GAT ACA GAA AAT      691
Ala Leu Asp Val Tyr Tyr Ala Lys Arg Leu Gly Val Asp Thr Glu Asn
100                 105                 110

CTA CTC GTT TCC CAA CCA AGC ACG GGC GAA GAA GCC TTA GAA ATT TTA      739
Leu Leu Val Ser Gln Pro Ser Thr Gly Glu Glu Ala Leu Glu Ile Leu
115                 120                 125                 130

GAA ACG ATC ACC AGA AGC GGA GGG ATT GAT TTA GTG GTG GTG GAT TCG      787
Glu Thr Ile Thr Arg Ser Gly Gly Ile Asp Leu Val Val Val Asp Ser
                135                 140                 145

GTG GCG GCC CTT ACG CCT AAA GCG GAG ATT GAT GGG GAT ATG GGC GAT      835
Val Ala Ala Leu Thr Pro Lys Ala Glu Ile Asp Gly Asp Met Gly Asp
            150                 155                 160

CAG CAT GTG GGC TTG CAA GCA AGG CTT ATG AGC CAT GCG TTA AGA AAA      883
Gln His Val Gly Leu Gln Ala Arg Leu Met Ser His Ala Leu Arg Lys
        165                 170                 175

ATC ACT GGT GTC TTG CAC AAG ATG AAC ACC ACT CTC ATT TTT ATC AAT      931
Ile Thr Gly Val Leu His Lys Met Asn Thr Thr Leu Ile Phe Ile Asn
    180                 185                 190

CAA ATA AGG ATG AAG ATC GGC ATG ACA GGT TAT GGG AGT CCA GAG ACC      979
Gln Ile Arg Met Lys Ile Gly Met Thr Gly Tyr Gly Ser Pro Glu Thr
195                 200                 205                 210

ACA ACC GGA GGC AAT GCC TTA AAA TTC TAT GCG AGC GTT AGG ATT GAT     1027
Thr Thr Gly Gly Asn Ala Leu Lys Phe Tyr Ala Ser Val Arg Ile Asp
```

|   |   |   |   |   |   |   |   |   |   |   |   |   |   |   |   |      |
|---|---|---|---|---|---|---|---|---|---|---|---|---|---|---|---|------|
|   |   |   | 215 |   |   |   |   | 220 |   |   |   |   | 225 |   |   |      |
| ATT | AGA | AGA | ATC | GCC | GCT | TTA | AAA | CAA | AAC | GAA | CAG | CAT | ATC | GGT | AAT | 1075 |
| Ile | Arg | Arg | Ile | Ala | Ala | Leu | Lys | Gln | Asn | Glu | Gln | His | Ile | Gly | Asn |      |
|     |     | 230 |     |     |     |     | 235 |     |     |     |     | 240 |     |     |     |      |
| AGG | GCT | AAA | GCT | AAA | GTC | GTT | AAA | AAT | AAA | GTC | GCT | CCG | CCC | TTT | AGA | 1123 |
| Arg | Ala | Lys | Ala | Lys | Val | Val | Lys | Asn | Lys | Val | Ala | Pro | Pro | Phe | Arg |      |
|     |     | 245 |     |     |     |     | 250 |     |     |     |     | 255 |     |     |     |      |
| GAA | GCG | GAA | TTT | GAC | ATC | ATG | TTT | GGG | GAA | GGG | ATT | TCT | AAA | GAG | GGC | 1171 |
| Glu | Ala | Glu | Phe | Asp | Ile | Met | Phe | Gly | Glu | Gly | Ile | Ser | Lys | Glu | Gly |      |
|     | 260 |     |     |     |     | 265 |     |     |     |     | 270 |     |     |     |     |      |
| GAA | ATC | ATT | GAC | TAT | GGT | GTG | AAA | TTA | GAC | ATC | GTG | GAT | AAG | AGC | GGG | 1219 |
| Glu | Ile | Ile | Asp | Tyr | Gly | Val | Lys | Leu | Asp | Ile | Val | Asp | Lys | Ser | Gly |      |
| 275 |     |     |     |     | 280 |     |     |     |     | 285 |     |     |     |     | 290 |      |
| GCA | TGG | CTT | AGC | TAC | CAG | GAT | AAA | AAG | CTA | GGG | CAA | GGC | CGA | GAA | AAC | 1267 |
| Ala | Trp | Leu | Ser | Tyr | Gln | Asp | Lys | Lys | Leu | Gly | Gln | Gly | Arg | Glu | Asn |      |
|     |     |     |     | 295 |     |     |     |     | 300 |     |     |     |     | 305 |     |      |
| GCT | AAA | GCC | TTA | TTG | AAA | GAA | GAT | AAA | GCG | CTA | GCG | AAT | GAA | ATC | ACT | 1315 |
| Ala | Lys | Ala | Leu | Leu | Lys | Glu | Asp | Lys | Ala | Leu | Ala | Asn | Glu | Ile | Thr |      |
|     |     |     | 310 |     |     |     |     | 315 |     |     |     |     | 320 |     |     |      |
| CTT | AAG | ATT | AAA | GAG | AGT | ATT | GGC | TCT | AAT | GAA | GAG | ATC | ATG | CCC | TTA | 1363 |
| Leu | Lys | Ile | Lys | Glu | Ser | Ile | Gly | Ser | Asn | Glu | Glu | Ile | Met | Pro | Leu |      |
|     |     | 325 |     |     |     |     | 330 |     |     |     |     | 335 |     |     |     |      |
| CCC | GAT | GAG | CCT | TTA | GAA | GAA | ATG | GAA | TAA | AAAGGATTTT | G | ATG | CTA | ACC |   | 1413 |
| Pro | Asp | Glu | Pro | Leu | Glu | Glu | Met | Glu | *   |            |   | Met | Leu | Thr |   |      |
|     | 340 |     |     |     |     | 345 |     |     |     |            |   | 1   |     |     |   |      |
| ATT | AAA | GAC | ATT | CAT | GCT | TTA | GAA | GTG | ATG | GAT | AGT | AGG | GGC | AAT | CCT | 1461 |
| Ile | Lys | Asp | Ile | His | Ala | Leu | Glu | Val | Met | Asp | Ser | Arg | Gly | Asn | Pro |      |
|     | 5   |     |     |     |     | 10  |     |     |     |     | 15  |     |     |     |     |      |
| ACC | ATT | CAA | GCC | AGC | GTG | ATT | TTA | AGC | GAT | AAC | ACT | AAG | GCG | AGT | GCG | 1509 |
| Thr | Ile | Gln | Ala | Ser | Val | Ile | Leu | Ser | Asp | Asn | Thr | Lys | Ala | Ser | Ala |      |
| 20  |     |     |     |     | 25  |     |     |     |     | 30  |     |     |     |     | 35  |      |
| ATT | GTG | CCT | AGC | GGG | GCG | AGC | ACC | GGT | AAA | AGA | GAG | GCG | TTA | GAA | TTA | 1557 |
| Ile | Val | Pro | Ser | Gly | Ala | Ser | Thr | Gly | Lys | Arg | Glu | Ala | Leu | Glu | Leu |      |
|     |     |     |     | 40  |     |     |     |     | 45  |     |     |     |     | 50  |     |      |
| AGG | GAT | AAT | GAC | AAA | ACC | CGT | TTT | TTG | GGT | AAA | GGG | GTT | TTA | AGG | GCA | 1605 |
| Arg | Asp | Asn | Asp | Lys | Thr | Arg | Phe | Leu | Gly | Lys | Gly | Val | Leu | Arg | Ala |      |
|     |     |     | 55  |     |     |     |     | 60  |     |     |     |     | 65  |     |     |      |
| TGC | GAA | AAT | GTC | AAT | AGC | GTG | ATC | AAA | CAC | CAT | TTA | ATA | GGG | CTT | GAA | 1653 |
| Cys | Glu | Asn | Val | Asn | Ser | Val | Ile | Lys | His | His | Leu | Ile | Gly | Leu | Glu |      |
|     |     | 70  |     |     |     |     | 75  |     |     |     |     | 80  |     |     |     |      |
| GCG | ACT | AAT | CAA | GCC | TTT | GTA | GAT | GAG | AGG | TTA | AGG | GCT | TTG | GAT | GGC | 1701 |
| Ala | Thr | Asn | Gln | Ala | Phe | Val | Asp | Glu | Arg | Leu | Arg | Ala | Leu | Asp | Gly |      |
|     | 85  |     |     |     |     | 90  |     |     |     |     | 95  |     |     |     |     |      |
| ACG | CCT | AAT | TAC | GCT | AAT | TTA | GGG | GCG | AAC | GCT | GTT | TTG | GGC | GTT | TCT | 1749 |
| Thr | Pro | Asn | Tyr | Ala | Asn | Leu | Gly | Ala | Asn | Ala | Val | Leu | Gly | Val | Ser |      |
| 100 |     |     |     |     | 105 |     |     |     |     | 110 |     |     |     |     | 115 |      |
| ATG | GCG | TTA | GCA | AGG | GCT | AGC | GCG | AAG | GCT | TTA | AAT | CTG | CCA | TTA | TAC | 1797 |
| Met | Ala | Leu | Ala | Arg | Ala | Ser | Ala | Lys | Ala | Leu | Asn | Leu | Pro | Leu | Tyr |      |
|     |     |     | 120 |     |     |     |     | 125 |     |     |     |     | 130 |     |     |      |
| CGC | TAT | TTA | GGG | GGG | GCT | AAC | GCT | CTG | ACT | TTA | CCT | GTG | CCG | ATG | CTC | 1845 |
| Arg | Tyr | Leu | Gly | Gly | Ala | Asn | Ala | Leu | Thr | Leu | Pro | Val | Pro | Met | Leu |      |
|     |     |     | 135 |     |     |     |     | 140 |     |     |     |     | 145 |     |     |      |
| AAT | ATC | ATC | AAC | GGC | GGA | ACG | CAT | GCG | AAC | AAT | TCC | ATA | GAC | TTC | CAA | 1893 |
| Asn | Ile | Ile | Asn | Gly | Gly | Thr | His | Ala | Asn | Asn | Ser | Ile | Asp | Phe | Gln |      |
|     |     | 150 |     |     |     |     | 155 |     |     |     |     | 160 |     |     |     |      |
| GAA | TAC | ATG | ATC | ATG | CCT | TTA | GGG | TTT | GAG | AGT | TTT | AAA | GAA |     |     | 1935 |
| Glu | Tyr | Met | Ile | Met | Pro | Leu | Gly | Phe | Glu | Ser | Phe | Lys | Glu |     |     |      |
|     | 165 |     |     |     |     | 170 |     |     |     |     | 175 |     |     |     |     |      |
| GC  |     |     |     |     |     |     |     |     |     |     |     |     |     |     |     | 1937 |

( 2 ) INFORMATION FOR SEQ ID NO:10:

( i ) SEQUENCE CHARACTERISTICS:
        ( A ) LENGTH: 347 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met Ala Ile Asp Glu Asp Lys Gln Lys Ala Ile Ser Leu Ala Ile Lys
 1               5                  10                  15

Gln Ile Asp Lys Val Phe Gly Lys Gly Ala Leu Val Arg Leu Gly Asp
                20                  25                  30

Lys Gln Val Glu Lys Ile Asp Ala Ile Ser Thr Gly Ser Leu Gly Leu
            35                  40                  45

Asp Leu Ala Leu Gly Ile Gly Gly Val Pro Lys Gly Arg Ile Ile Glu
        50                  55                  60

Ile Tyr Gly Pro Glu Ser Ser Gly Lys Thr Thr Leu Ser Leu His Ile
 65                  70                  75                  80

Ile Ala Glu Cys Gln Lys Asn Gly Gly Val Cys Ala Phe Ile Asp Ala
                85                  90                  95

Glu His Ala Leu Asp Val Tyr Tyr Ala Lys Arg Leu Gly Val Asp Thr
                100                 105                 110

Glu Asn Leu Leu Val Ser Gln Pro Ser Thr Gly Glu Glu Ala Leu Glu
            115                 120                 125

Ile Leu Glu Thr Ile Thr Arg Ser Gly Gly Ile Asp Leu Val Val Val
        130                 135                 140

Asp Ser Val Ala Ala Leu Thr Pro Lys Ala Glu Ile Asp Gly Asp Met
145                 150                 155                 160

Gly Asp Gln His Val Gly Leu Gln Ala Arg Leu Met Ser His Ala Leu
                165                 170                 175

Arg Lys Ile Thr Gly Val Leu His Lys Met Asn Thr Thr Leu Ile Phe
                180                 185                 190

Ile Asn Gln Ile Arg Met Lys Ile Gly Met Thr Gly Tyr Gly Ser Pro
            195                 200                 205

Glu Thr Thr Thr Gly Gly Asn Ala Leu Lys Phe Tyr Ala Ser Val Arg
210                 215                 220

Ile Asp Ile Arg Arg Ile Ala Ala Leu Lys Gln Asn Glu Gln His Ile
225                 230                 235                 240

Gly Asn Arg Ala Lys Ala Lys Val Val Lys Asn Lys Val Ala Pro Pro
                245                 250                 255

Phe Arg Glu Ala Glu Phe Asp Ile Met Phe Gly Glu Gly Ile Ser Lys
                260                 265                 270

Glu Gly Glu Ile Ile Asp Tyr Gly Val Lys Leu Asp Ile Val Asp Lys
            275                 280                 285

Ser Gly Ala Trp Leu Ser Tyr Gln Asp Lys Lys Leu Gly Gln Gly Arg
        290                 295                 300

Glu Asn Ala Lys Ala Leu Leu Lys Glu Asp Lys Ala Leu Ala Asn Glu
305                 310                 315                 320

Ile Thr Leu Lys Ile Lys Glu Ser Ile Gly Ser Asn Glu Glu Ile Met
                325                 330                 335

Pro Leu Pro Asp Glu Pro Leu Glu Glu Met Glu
                340                 345
```

( 2 ) INFORMATION FOR SEQ ID NO:11:

( i ) SEQUENCE CHARACTERISTICS:
    ( A ) LENGTH: 177 amino acids
    ( B ) TYPE: amino acid
    ( D ) TOPOLOGY: linear ( i i ) MOLECULE TYPE: protein ( x i ) SEQUENCE DESCRIPTION: SEQ ID NO:11:

| | | | | | | | | | | | | | | | |
|---|---|---|---|---|---|---|---|---|---|---|---|---|---|---|---|
| Met | Leu | Thr | Ile | Lys | Asp | Ile | His | Ala | Leu | Glu | Val | Met | Asp | Ser | Arg |
| 1 | | | | 5 | | | | | 10 | | | | | 15 | |
| Gly | Asn | Pro | Thr | Ile | Gln | Ala | Ser | Val | Ile | Leu | Ser | Asp | Asn | Thr | Lys |
| | | | 20 | | | | | 25 | | | | | 30 | | |
| Ala | Ser | Ala | Ile | Val | Pro | Ser | Gly | Ala | Ser | Thr | Gly | Lys | Arg | Glu | Ala |
| | | 35 | | | | | 40 | | | | | 45 | | | |
| Leu | Glu | Leu | Arg | Asp | Asn | Asp | Lys | Thr | Arg | Phe | Leu | Gly | Lys | Gly | Val |
| | 50 | | | | 55 | | | | | | 60 | | | | |
| Leu | Arg | Ala | Cys | Glu | Asn | Val | Asn | Ser | Val | Ile | Lys | His | His | Leu | Ile |
| 65 | | | | | 70 | | | | | 75 | | | | | 80 |
| Gly | Leu | Glu | Ala | Thr | Asn | Gln | Ala | Phe | Val | Asp | Glu | Arg | Leu | Arg | Ala |
| | | | | 85 | | | | | 90 | | | | | 95 | |
| Leu | Asp | Gly | Thr | Pro | Asn | Tyr | Ala | Asn | Leu | Gly | Ala | Asn | Ala | Val | Leu |
| | | | 100 | | | | | 105 | | | | | 110 | | |
| Gly | Val | Ser | Met | Ala | Leu | Ala | Arg | Ala | Ser | Ala | Lys | Ala | Leu | Asn | Leu |
| | | 115 | | | | | 120 | | | | | 125 | | | |
| Pro | Leu | Tyr | Arg | Tyr | Leu | Gly | Gly | Ala | Asn | Ala | Leu | Thr | Leu | Pro | Val |
| | 130 | | | | | 135 | | | | | 140 | | | | |
| Pro | Met | Leu | Asn | Ile | Ile | Asn | Gly | Gly | Thr | His | Ala | Asn | Asn | Ser | Ile |
| 145 | | | | | 150 | | | | | 155 | | | | | 160 |
| Asp | Phe | Gln | Glu | Tyr | Met | Ile | Met | Pro | Leu | Gly | Phe | Glu | Ser | Phe | Lys |
| | | | | 165 | | | | | 170 | | | | | 175 | |
| Glu | | | | | | | | | | | | | | | |

NUCLEIC ACID ENCODING *HELICOBACTER PYLORI* ENOLASE

This is a continuation-in-part of application Ser. No. 08/215,928, filed: Mar. 21, 1994 issued as U.S. Pat. No. 5,434,253 on Jul. 18, 1995.

This work was supported by National Institutes of Health grant R01CA58834. The government has certain rights in the invention.

BACKGROUND OF THE INVENTION

It has previously been established that genes such as recA are involved in recombination in bacteria, which contributes to intra- and intergenic variation. Intragenic variation is thought to be important for bacterial growth. Bacterial RecA proteins are important in recombinational repair of damaged DNA, in bacterial response to environmental stress (e.g., SOS), and also in functions such as DNA transformation and chromosomal rearrangement that are involved in bacterial pathogenesis. Nothing is known of the existence or role of recombinase in *H. pylori*, and no *H. pylori* recA gene has been identified.

*Helicobacter pylori* is the major causative agent of chronic superficial gastritis in humans, and infection with this organism is an important etiologic factor in the pathogenesis of peptic ulcer disease and possibly gastric cancer (20–22). In terms of human suffering and financial burden, *H. pylori* infection is very costly. There is no vaccine or fully effective treatment for *H. pylori* infection.

The development of a vaccine against *H. pylori* infection is highly desirable. Live vaccine strains would be very useful, since chemical purification of large amounts of *H. pylori* antigens is likely to be expensive and subject to variation between batches of antigen. The alternative of being able to directly immunize humans with an attenuated *H. pylori* strain is, therefore, attractive, and could provide a more effective and inexpensive means of achieving immunity to *H. pylori* infection. Such a vaccine, if comprising a live attenuated bacterium should not be susceptible to reversion to the wild type. The present invention meets this need by providing the *H. pylori* recA gene and mutant strains and methods of making mutant strains of *H. pylori* that have been genetically altered so that no functional recombinase is produced.

SUMMARY OF THE INVENTION

An isolated nucleic acid encoding the *Helicobacter pylori* recombinase is provided. The nucleic acid can comprise the nucleotide sequence defined in the Sequence Listing as SEQ ID NO:1. The nucleic acid can consist of nucleotides 350 through 1393 in the nucleotide sequence defined in the Sequence Listing as SEQ ID NO:9. Also provided is an isolated nucleic acid that selectively hybridizes with the recombinase-encoding nucleic acid under stringent conditions and is at least 70% complementary with the segment and strand of the nucleic acid of SEQ ID NO:1 to which it hybridizes. The recombinase-encoding nucleic acid and selectively hybridizing nucleic acids of the invention can be in a vector suitable for expressing the nucleic acid or portion of thereof. The nucleic acid in a vector can be in a host suitable for expressing the nucleic acid.

The invention also provides an isolated nucleic acid encoding a *Helicobacter pylori* enolase. The nucleic acid can comprise nucleotides 1405 through 1937 in the nucleotide sequence defined in the Sequence Listing as SEQ ID NO:9. Also provide is an isolated nucleic acid encoding a portion of the *Helicobacter pylori* enolase, consisting of nucleotides 1405 through 1937 in the nucleotide sequence defined in the Sequence Listing as SEQ ID NO:9. Also provided is an isolated nucleic acid that hybridizes with the enolase-encoding nucleic acid under stringent conditions and is at least 70% complementary with the segment and strand of the nucleic acid of SEQ ID NO:9 to which it hybridizes. The enolase-encoding nucleic acid and selectively hybridizing nucleic acids of the invention can be in a vector suitable for expressing the nucleic acid or portion of thereof. The nucleic acid in a vector can be in a host cell that can express the nucleic acid.

Having discovered the existence of a recombinase in *H. pylori*, the invention also provides a mutant strain of *H. pylori* that does not express a functional recombinase (recA⁻ mutant). The mutant can either not express recombinase or express a non-functioning recombinase. The recA⁻ mutants are more sensitive to acidic pH than are the wild-type *H. pylori*. Thus, the invention provides a method of inducing acid sensitivity in *H. pylori*, comprising mutating the *H. pylori* so that it does not express a functional recombinase, the absence of a functioning recombinase resulting in increased acid sensitivity.

An immunogenic amount of the recA⁻ mutant *H. pylori* in a pharmaceutically acceptable carrier can be used as a vaccine. A method of immunizing a subject against infection by *H. pylori* comprises administering to the subject an immunogenic amount of mutant *H. pylori* in a carrier for the mutant.

Having discovered the existence of an enolase in *H. pylori*, a mutant strain of *H. pylori* that does not express a functional enolase is also provided. An immunogenic amount of the mutant *H. pylori* that does not express a functional enolase can is provided in a pharmaceutically acceptable carrier. This composition can be used in a method of immunizing a subject against infection by *H. pylori*, comprising administering to the subject the immunogenic amount of enolase⁻ mutant *H. pylori*.

BRIEF DESCRIPTION OF THE FIGURES

FIG. 2A shows the acid sensitivity of recA mutants in the presence of 10 mM urea.

DETAILED DESCRIPTION OF THE INVENTION

Nucleic Acids

Figure 1:
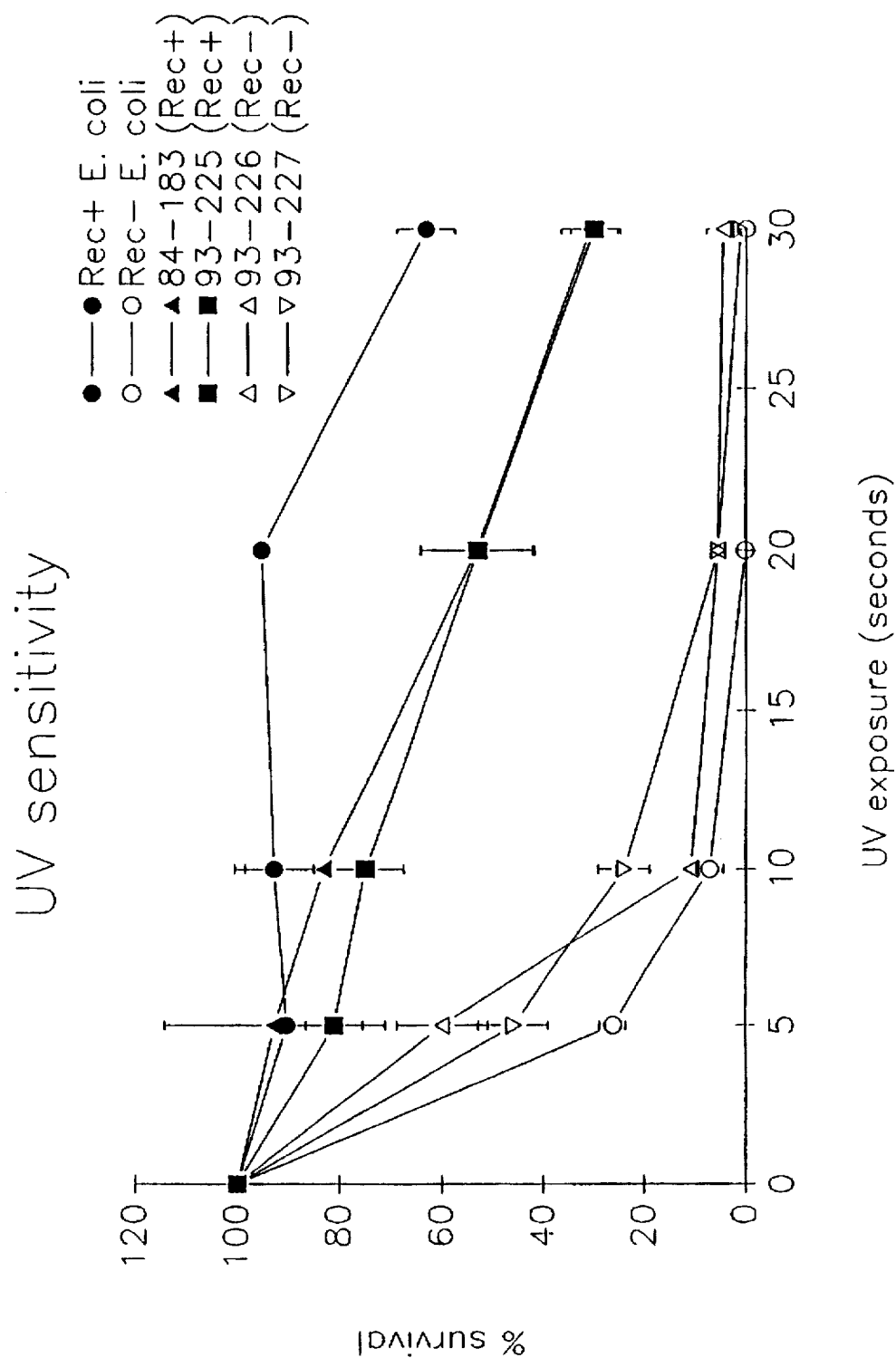
FIG. 1 shows the UV sensitivity of recA mutants.

An isolated nucleic acid encoding the *Helicobacter pylori* recombinase is provide. "Isolated" means separated from other genes of *H. pylori*. The nucleic acid can comprise the nucleotide sequence defined in the Sequence Listing as SEQ ID NO:1. The nucleic acid of SEQ ID NO:1 is a double stranded partial sequence of the recombinase gene. The nucleic acid can consist of nucleotides 350 through 1393 in the nucleotide sequence defined in the Sequence Listing as SEQ ID NO:9 or alternative coding sequences for the amino acids shown in the sequence. The nucleic acid of SEQ ID NO:9 is a double stranded entire sequence of the recombinase gene. Given the present disclosure of the *H. pylori* recombinase gene, the skilled artisan can routinely obtain and sequence the gene in any strain of *H. pylori*.

The invention also provides an isolated nucleic acid encoding a *Helicobacter pylori* enolase. The nucleic acid can comprise nucleotides 1405 through 1937 in the nucleotide sequence defined in the Sequence Listing as SEQ ID NO:9 or an alternative coding sequence for the corresponding amino acids 1 through 177 of SEQ ID NO:11. Also provided is an isolated nucleic acid encoding a portion of the *Helicobacter pylori* enolase, consisting of nucleotides 1405 through 1937 in the nucleotide sequence defined in the Sequence Listing as SEQ ID NO:9.

Also provided is an isolated nucleic acid of at least 10 nucleotides that selectively hybridizes with the nucleic acid encoding the *H. pylori* recombinase under stringent conditions and has at least 70% complementarity with the segment and strand of the nucleic acid to which it hybridizes. Further provided is an isolated nucleic acid of at least 10 nucleotides that hybridizes with the nucleic acid consisting of nucleotides 350 through 1393 or alternative coding sequences for the corresponding amino acids in the nucleotide sequence defined in the Sequence Listing as SEQ ID NO:9 under stringent conditions, has at least 70% complementarity with the segment of the nucleic acid to which it hybridizes. The hybridizing nucleic acid can encode a *Helicobacter pylori* recombinase or a portion thereof. Hybridization under these conditions is considered to be selective.

The invention also provides an isolated nucleic acid of at least 10 nucleotides that hybridizes with the nucleic acid consisting of nucleotides 1405 through 1937 or alternative coding sequences for the corresponding amino acids in the nucleotide sequence defined in the Sequence Listing as SEQ ID NO:9 under stringent conditions and has at least 70% complementarity with the segment of the nucleic acid to which it hybridizes. Hybridization under these conditions is considered to be selective. The hybridizing nucleic acid can encode a *Helicobacter pylori* enolase or a portion thereof.

The hybridizing nucleic acids can be used, for example, as probes or primers for detecting the presence of an organism that has the nucleic acid to which it hybridizes. Thus, the invention provides a method of detecting *Helicobacter pylori* infection in a subject, comprising detecting the presence of the selectively hybridizing nucleic acid in a specimen from the subject, the presence of the nucleic acid indicating infection with *Helicobacter pylori*. Alternatively, the selectively hybridizing nucleic acid can encode a polypeptide, and, can thereby be placed in a vector and host to produce the protein it encodes, a functionally similar protein, an antigenic fragment or a fragment exhibiting the protein's function.

As used herein to describe nucleic acids, the term "selectively hybridizes" excludes the occasional randomly hybridizing nucleic acids as well as nucleic acids that encode other known homologs of the present proteins. The selectively hybridizing nucleic acids of the invention can have at least 70%, 80%, 85%, 90%, 95%, 97%, 98% and 99% complementarity with the segment and strand of the sequence to which it hybridizes. The nucleic acids can be at least 10, 18, 50, 100, 150, 200, 300, 500, 750, 1000 or 2000 nucleotides in length. Thus, the nucleic acid can be an alternative coding sequence for the protein, or can be used as a probe or primer for detecting the presence *H pylori*. If used as primers, the invention provides compositions including at least two nucleic acids which selectively hybridize with different regions so as to amplify a desired region. Depending on the length of the probe or primer, it can range between 70% complementary bases and full complementarity and still hybridize under stringent conditions. For example, for the purpose of diagnosing the presence of *H. pylori*, the degree of complementarity between the hybridizing nucleic acid (probe or primer) and the sequence to which it hybridizes (*H. pylori* DNA from a sample) should be at least enough to exclude hybridization with a nucleic acid from a related bacterium. Thus, a nucleic acid that selectively hybridizes with a *H. pylori* recombinase or enolase coding sequence will not selectively hybridize under stringent conditions with a nucleic acid for that protein in another species, and vice versa. The invention provides examples of these nucleic acids of *H. pylori*, so that the degree of complementarity required to distinguish selectively hybridizing from nonselectively hybridizing nucleic acids under stringent conditions can be clearly determined for each nucleic acid. It should also be clear that the hybridizing nucleic acids of the invention will not hybridize with nucleic acids encoding unrelated proteins (hybridization is selective).

"Stringent conditions" refers to the washing conditions used in a hybridization protocol. In general, the washing conditions should be a combination of temperature and salt concentration chosen so that the denaturation temperature is approximately 5°–20° C. below the calculated $T_m$ of the hybrid under study. The temperature and salt conditions are readily determined empirically in preliminary experiments in which samples of reference DNA immobilized on filters are hybridized to the probe or protein coding nucleic acid of interest and then washed under conditions of different stringencies. For example, the 470 bp recA PCR fragment (described below) is used as a specific radiolabeled probe for *H. pylori* recA by performing hybridizations at 68° C. in the presence of 5× SSPE (12), then removing non-specific hybrids by high-stringency washes of 0.1× SSPE at 68° C. as described in reference 12, chapter 9. Hybridizations with oligonucleotide probes shorter than 18 nucleotides in length are done at 5°–10° C. below the estimated $T_m$ in 6× SSPE, then washed at the same temperature in 2× SSPE as described in reference 12, chapter 11. The $T_m$ of such an oligonucleotide can be estimated by allowing 2° C. for each A or T nucleotide, and 4° C. for each G or C. An 18 nucleotide probe of 50% G+C, would, therefore, have an approximate $T_m$ of 54° C.

One skilled in the art can readily obtain the nucleic acids of the present invention using routine methods to synthesize a full gene as well as shorter nucleotide fragments. For example, techniques for obtaining nucleic acids such as those provided in the Sequence Listing are specifically provided in the application. Furthermore, additional methods are provided in the art that can be utilized without significant modification. Ferretti et al. (*Proc. Natl. Acad. Sci.* 82:599–603 (1986)) and Wosnick et al. (*Gene* 76:153–160 (1989)) show routine methods to synthesize a gene of known sequence. More specifically, Ferretti et al. teach the synthesis of a 1057 base pair synthetic bovine rhodopsin gene from synthetic oligonucleotides. The synthesized gene was faithful to the known sequence (first sentence, page 603), demonstrating the reliability of this method of gene synthesis.

Additionally, Wosnick et al. teach the synthesis of a maize glutathione-transferase (GST) gene using an efficient, one-step annealing/ligation protocol. This technique also produced a complete synthetic gene with 100% fidelity, which demonstrates the routine nature of this protocol.

Given the teaching in Example 1 it was routine to determine the rest of the sequence of the recombinase gene (see Example 2). For example, the 3' end of the recA gene can be cloned and its DNA sequence determined in a manner similar to that used in isolating the 5' end of the gene. Namely, a specific chromosomal DNA fragment can be predicted to contain the 3' end of the recA gene by Southern hybridization analysis. This fragment can then be isolated from a genomic library of *H. pylori* 84-183 DNA prepared in λZAPII using chromosomal DNA digested with the desired restriction enzyme. Identification and isolation of the desired recombinant clone would be achieved following hybridization with a recA-specific probe as described above. DNA sequence analysis of this clone would provide the sequence of the remainder of the recA gene.

Vectors and Hosts

The protein-encoding nucleic acids and selectively hybridizing nucleic acids of the invention can be in a vector suitable for expressing the nucleic acid. The nucleic acid in a vector can be in a host suitable for expressing the nucleic acid.

There are numerous *E. coli* expression vectors known to one of ordinary skill in the art useful for the expression of the antigen. Other microbial hosts suitable for use include bacilli, such as *Bacillus subtilus*, and other enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with am operator sequence, and have ribosome binding site sequences for example, for initiating and completing transcription and translation. If necessary an amino terminal methionine can be provided by insertion of a Met codon 5' and in-frame with the antigen. Also, the carboxy-terminal extension of the antigen can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carried out by yeast secretory systems. The *Saccharomyces cerevisiae* pre-pro-alpha-factor leader region (encoded by the MFα-1 gene) is routinely used to direct protein secretion from yeast (Brake et al., 1984). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage-signal sequence. The antigen coding sequence can be fused in-frame to the pre-pro-alpha-factor leader region. This construct is then put under the control of a strong transcription promoter, such as the alcohol dehydrogenase I promoter or a glycolytic promoter. The antigen coding sequence is followed by a translation termination codon which is followed by transcription termination signals. Alternatively, the antigen coding sequences can be fused to a second protein coding sequence, such as Sj26 or β-galactosidase, used to facilitate purification of the fusion protein by affinity chromatography. The insertion of protease cleavage sites to separate the components of the fusion protein is applicable to constructs used for expression in yeast.

Mammalian cells permit the expression of proteins in an environment that favors important post-translational modifications such as folding and cysteine pairing, addition of complex carbohydrate structures, and secretion of active protein. Vectors useful for the expression of antigen in mammalian cells are characterized by insertion of the antigen coding sequence between a strong viral promoter and a polyadenylation signal. The vectors can contain genes conferring either gentamicin or methotrexate resistance for use as selectable markers. The antigen and immunoreactive fragment coding sequence can be introduced into a Chinese hamster ovary cell line using a methotrexate resistance-encoding vector. Presence of the vector DNA in transformed cells can be confirmed by Southern analysis and production of an RNA corresponding to the antigen coding sequence can be confirmed by Northern analysis. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the DNA segments of interest can be transferred into the host cell by well-known methods, which vary depending on the type of cellular host. For example, calcium chloride transfection is commonly utilized for prokaryotic cells, whereas calcium phosphate treatment or electroporation can be used for other cellular hosts.

Alternative vectors for the expression of antigen in mammalian cells, those similar to those developed for the expression of human gamma-interferon, tissue plasminogen activator, clotting Factor VIII, hepatitis B virus surface antigen, protease NexinI, and eosinophil major basic protein, can be employed. Further, the vector can include CMV promoter sequences and a polyadenylation signal available for expression of inserted DNAs in mammalian cells (such as COS7).

The DNA sequences can be expressed in hosts after the sequences have been operably linked to, i.e., positioned to ensure the functioning of, an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired DNA sequences (see, e.g., U.S. Pat. No. 4,704,362).

Polynucleotides encoding a variant polypeptide can include sequences that facilitate transcription (expression sequences) and translation of the coding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

Mutant Organism

Having discovered the existence of a recombinase in *H. pylori*, the invention also provides a genetically altered mutant strain of *H. pylori* that does not express a functional recombinase (recA⁻ mutant). The mutant can either not express recombinase or express a non-functioning recombinase. In one example, the mutant *H. pylori* strain is obtained by making an insertion substitution mutation in the coding sequence for the recombinase as described in the Examples. Since the present invention provides the nucleic acid encoding the recombinase, other methods of mutating the coding sequence of the recombinase can be used to obtain other mutant strains as contemplated herein.

An example of the recA deficient mutant *H. pylori* strain of the present invention is designated 93-226 and is deposited with the American Type Culture Collection (1230 Parklawn Drive, Rockville, Md. 20852) under ATCC Accession Number 55541. A further example of a recA deficient mutant *H. pylori* strain of the present invention is designated 93-227 and is deposited with the American Type Culture Collection under ATCC Accession Number 55542.

Additional mutants can be prepared, for example, by inserting a nucleic acid in the recA gene or deleting a portion of the recA gene so as to render the gene non-functional or protein produced in such low amounts that the organism is non-infectious or attenuated. Furthermore, by providing the nucleotide sequence for the nucleic acid encoding the recombinase, the present invention permits the making of specific point mutations having the desired effect. The deletion, insertion or substitution mutations can be made in either the regulatory or coding region to prevent transcription or translation or to render the transcribed and translated product nonfunctional.

One such approach to the construction of a deletion or insertion mutant is via the Donnenberg method (Donnenberg and Kaper *Infect. Immun.* 4310–4317, 1991). A deletion in recA is created by deleting a restriction fragment and religating the clone. This mutant is cloned into suicide vector pILL570. The sacB gene of *Bacillus subtilis* is also cloned into the suicide vector to provide a conditionally lethal phenotype. This construct is transformed into *H. pylori* by electroporation, and transformants selected by spectinomycin resistance. The merodiploid strain which contains the suicide vector and the mutated version of the recA gene are exposed to sucrose to directly select for organisms that have undergone a second recombination, resulting in the loss of the vector. These and other well known methods of making mutations can be applied to the nucleic acids provided herein to obtain other desired mutations. Included are insertional mutagenesis as described in reference 8, as well as linker-scanning mutagenesis (23) and site-directed mutagenesis (24).

Non-isogenic mutants are also within the scope of the invention. For example, a live attenuated *H. pylori* that is also a recA⁻ mutant according to the present invention, is provided. A recA⁻cagA⁻ mutant strain is constructed, for example, by insertion mutation of both the cagA and recA genes, according to the methods taught herein and taught in U.S. application Ser. No. 08/053,614, which describes the generation of a cagA⁻ (referred to therein as tagA) mutant. A recA⁻vacA⁻ mutant strain is constructed, for example, by insertion mutation of both the recA and vacA genes, according to the methods taught herein. A recA⁻cagA⁻vacA⁻ mutant strain is constructed, for example, by insertion mutation of the recA, cagA and vacA genes, according to the methods taught herein for recA and vacA, and taught in U.S. application Ser. No. 08/053,614, which describes the generation of a cagA mutant. Any of the well known methods of mutating a gene can be used in the present invention to generate *H. pylori* mutant strains. The strains can be tested as provided for immunogenicity.

A mutant strain of *H. pylori* that does not express a functional enolase is also provided. An example of an eno⁻ mutant is described in Example 2. The eno⁻ mutant can be constructed by any of the methods described above for the recA⁻ mutant. As with the recA mutants described above the enolase mutant can be isogenic or non-isogenic. Non-isogenic eno⁻ mutants can be made that include cagA, vacA or recA or combinations thereof as described above. Preferably, all the other desired mutations will be made before the recA or eno mutations. Given the teaching herein, other eno⁻ mutants can be routinely constructed as described above and in the examples.

The recA⁻ and eno⁻ mutants are more sensitive to acidic pH than are the wild-type *H. pylori*. Thus, the invention provides a method of inducing acid sensitivity in *H. pylori*, comprising mutating the *H. pylori* so that it does not express a functional recombinase or mutating the *H. pylori* so that it does not express a functional enolase or making both mutations. The absence of a functioning recombinase or a functioning enolase results in increased acid sensitivity. Such a method of generating a mutant *H. pylori* and measuring its acid sensitivity are provided in the Examples.

The recA⁻ and eno⁻ mutants are more sensitive to ultraviolet light than are the wild-type *H. pylori*. Thus, the invention provides a method of inducing ultraviolet light sensitivity in *H. pylori*, comprising mutating the *H. pylori* so that it does not express a functional recombinase or mutating the *H. pylori* so that it does not express a functional enolase or making both mutations. The absence of a functioning recombinase or a functioning enolase results in increased UV light sensitivity. Such a method of generating a mutant *H. pylori* and measuring its UV light sensitivity are provided in the Examples.

The recA⁻ and eno⁻ mutants are more sensitive to antimicrobial agents than are the wild-type *H. pylori*. Thus, the invention provides a method of enhancing *H. pylori* sensitivity to antimicrobial agents, comprising mutating the *H. pylori* so that it does not express a functional recombinase or mutating the *H. pylori* so that it does not express a functional enolase or making both mutations. The absence of a functioning recombinase or a functioning enolase results in enhanced sensitivity to antimicrobial agents. Such a method of generating a mutant *H. pylori* and measuring its sensitivity to antimicrobial agents are provided in the Examples. The enhanced susceptibilities of these recA⁻ strains and eno⁻ strains to antimicrobial agents make them preferred as candidates for live vaccine strains, since this would facilitate their eradication upon completion of a vaccination regimen; the heightened (approximately two-log) susceptibility to metronidazole is expected to be particularly useful.

Vaccines

An immunogenic amount of the recA⁻ mutant *H. pylori* in a pharmaceutically acceptable carrier can be used as a vaccine. A method of immunizing a subject against infection by *H. pylori* comprises administering to the subject an immunogenic amount of mutant *H. pylori* in a carrier for the mutant.

Work with animal models indicates that it should be possible to elicit a protective immune response by vaccinating humans with *H. pylori* antigens (e.g. urease or flagella). Thus, a live, attenuated *H. pylori* vaccine strains should be attainable. The ideal attenuated *H. pylori* strain is one that is able to survive long enough to elicit a protective mucosal immune response before eradication of the vaccine strain by the host. This strain can be engineered so as to express large amounts of antigens (e.g., urease or flagellar subunits) in a form that elicits a protective response such as is seen in animal models (37, 38), while at the same time preserving the genetic integrity of the vaccine strain. *H. pylori* recA mutants, possibly in combination with mutations in other *H. pylori* genes such as vacA or cagA, should meet these criteria of good vaccine strains. The initial results suggest that not only are *H. pylori* recA mutants attenuated in mice, but they also appear to be completely deficient in natural transformation. Deficiency in RecA function is also expected to eliminate the possibility of reversion of these strains to virulence, and should prevent uptake of DNA from neighboring cells as well as genetic rearrangement that might diminish their antigenicity.

The recA$^-$ mutants are well suited for use as a vaccine. Because of the increased acid sensitivity of the mutants, the mutant can be introduced into the stomach of the subject and remain long enough to stimulate an immune response, but will die before significant disease resulting from infection occurs.

Furthermore, because recombinase plays a role in genetic variability, the mutants of the invention are genetically more stable than wild-type *H. pylori*. Thus, a live attenuated *H. pylori* that is also a recA$^-$ mutant according to the present invention, is less likely to revert to virulence than a recA$^+$ *H. pylori*.

An immunogenic amount of the mutant *H. pylori* that does not express a functional enolase is provided in a pharmaceutically acceptable carrier. This composition can be used in a method of immunizing a subject against infection by *H. pylori*, comprising administering to the subject the immunogenic amount of enolase$^-$ mutant *H. pylori*.

Determining immunogenicity

The isolated mutant strains of the invention can be tested to determine their immunogenicity. Briefly, various concentrations of a putative immunogen are prepared and administered to an animal and the immunological response (e.g., the production of antibodies or cell mediated immunity) of an animal to each concentration is determined. The amounts of antigen administered depend on the subject, e.g. a human or a guinea pig, the condition of the subject, the size of the subject, etc. Thereafter, an animal so inoculated with the strain can be exposed to the bacterium to test the potential vaccine effect of the specific immunogenic protein or fragment.

For example, recently described mouse models can be used to test vaccine strains for immunogenicity and protective response (37,38). Also, a well-established model is that of gnotobiotic piglets, in which the recA mutant strain is first fed to the piglets can also be used to test vaccines. After a suitable interval, the clearance of the vaccine strain is evaluated. Next, this piglet is challenged with the wild-type strain and the presence or absence of infection is ascertained (25,26).

Once immunogenicity is established as described above, immunogenic amounts of the antigen can be determined using standard procedures. Briefly, immunogenic amounts of a recA$^-$ mutant of the invention can be determined using standard procedures. Briefly, various concentrations of the recA$^-$ mutant are prepared, administered to an animal and the immunological response (e.g., the production of antibodies) of an animal to each concentration is determined.

Pharmceutically acceptable carrier

The pharmaceutically acceptable carrier in the vaccine of the instant invention can comprise saline or other suitable carriers (Arnon, R. (Ed.) *Synthetic Vaccines* I:83–92, CRC Press, Inc., Boca Raton, Fla., 1987). An adjuvant can also be a part of the carrier of the vaccine, in which case it can be selected by standard criteria based on the antigen used, the mode of administration and the subject (Arnon, R. (Ed.), 1987). Methods of administration can be by oral or sublingual means, or by injection, depending on the particular vaccine used and the subject to whom it is administered.

It can be appreciated from the above that the vaccine can be used as a prophylactic or a therapeutic modality, for example, by inducing a therapeutic immune response. Thus, the invention provides methods of preventing or treating *H. pylori* infection and the associated diseases by administering the vaccine to a subject.

Delivery of Foreign Antigens

Furthermore, attenuated *H. pylori* strains useful for delivering *H. pylori* antigens in a manner that elicits a protective mucosal immune response can be useful for delivering foreign antigens as well. Delivery of foreign antigens in a recA$^-$, attenuated *H. pylori* strain would be performed similar to delivery of native *H. pylori* antigens, namely, by engineering these *H. pylori* strains, using standard methods, to contain nucleic acids (either in the chromosome or on *H. pylori* shuttle plasmids) which express the foreign antigen of interest. Foreign antigens can be nucleic acids, proteins, glycoproteins or other antigenic structures derived from bacteria or viruses that cause any of numerous diseases, including tuberculosis, salmonellosis, cholera, pertussis, AIDS, and even emerging diseases such as Ebola. Deficiency in RecA function is also expected to prevent natural transformation, to eliminate the possibility of reversion of these strains to virulence, and should prevent uptake of DNA from neighboring cells as well as genetic rearrangement that might diminish the antigenicity of the foreign antigen.

Thus, the present invention provides a genetically altered mutant strain of *H. pylori* that does not express a functional recombinase, further comprising a non-*H. pylori* nucleic acid. The invention also provides a method of delivering a foreign nucleic acid to a subject by administering to the subject an amount of the recA$^-$ mutant with the foreign nucleic acid.

EXAMPLE 1

Strains and growth conditions.

Strains and plasmids used in this study are listed in Table 1. *E. coli* were routinely grown in LB broth or agar (12) supplemented with carbenicillin (100 µg/ml), kanamycin (30 µg/ml), and/or chloramphenicol (30 µg/ml) when appropriate. *H. pylori* strains were grown on blood agar plates at 37° C. in an atmosphere of 5% $CO_2$/95% air. Antibiotic-resistant *H. pylori* were selected with 30 µg/ml kanamycin or 15 µg/ml chloramphenicol.

TABLE 1

Strains/plasmids used in this study.

| Strain/plasmid | Relevant genotype | Reference |
|---|---|---|
| *E. coli* | | |
| Y1089 | recA$^+$ | (19) |
| DH5αMCR | recA1 | (6) |
| *H. pylori* | | |
| 84-183 (ATCC 53726) | recA$^+$ | (9) |
| 93-225 | recA$^+$cagA::km | Ex. 1 |
| 93-226 (ATCC 55541) | recA::km | Ex. 1 |

TABLE 1-continued

Strains/plasmids used in this study.

Figure 2B:
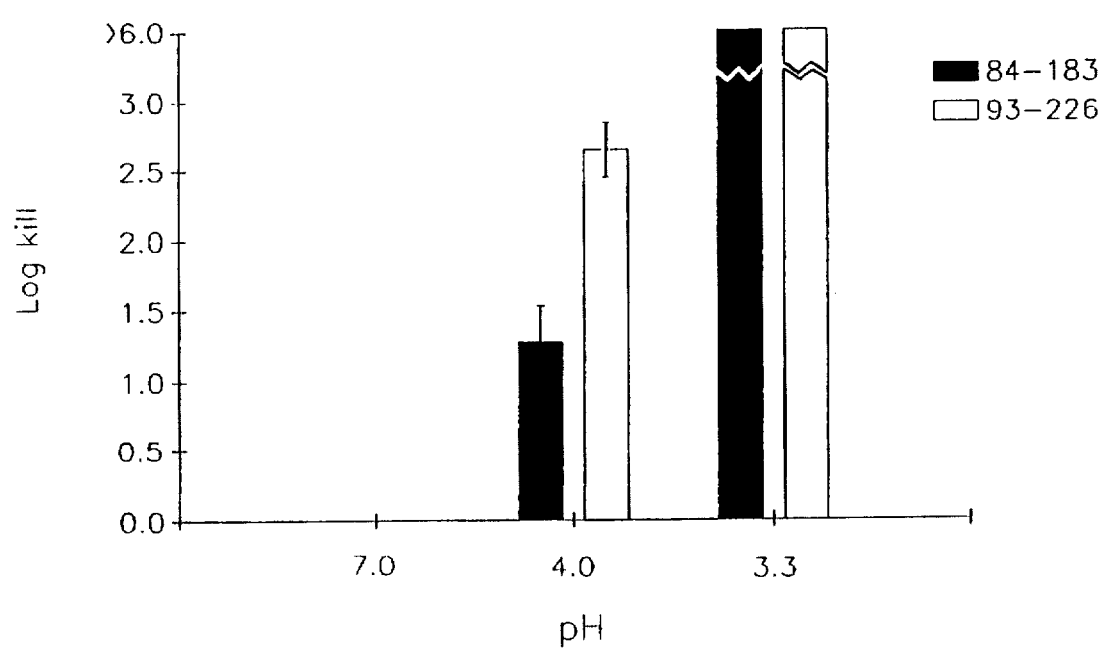
FIG. 2B shows the acid sensitivity of recA mutants in the absence of urea.

| Strain/plasmid | Relevant genotype | Reference |
|---|---|---|
| 93-227 (ATCC 55542) | recA::cm | Ex. 1 |
| 94-49 | eno::km | Ex. 2 |
| Plasmids | | |
| pSAT101 | recA (5' end) | Ex. 1 |
| pSAT104 | recA (3' end) | Ex. 2 |
| pSAT105 | recA (reconstructed) | Ex. 2 |
| PCR primers | | |
| Degenerate | Amino acid Sequence | |
| RecaF | E1(Y/F)GPE | |
| rec2R | NALKFYA | |
| Non-degenerate | Location in FIG. 2 | |
| Rec101 | 539–558 | |
| Rec102 | 908–928 (complement) | |
| Rec112 | 1052–1071 | |
| Eno101 | 1631–1651 | |
| Eno104 | 1479–1500 (complement) | |
| Eno-R | 1912–1933 (complement) | |
| km-F | — | |
| km-R | — | |

DNA techniques.

Restriction enzymes and Klenow fragment of *E. coli* DNA polymerase I were purchased either from New England Biolabs (Beverly, Mass.) or from Promega (Madison, Wis.), and were used according to manufacturer's directions. *H. pylori* chromosomal DNA was prepared as previously described (14). Hybridizations were done as previously described (2), using $^{32}$P-labeled probes made by random-priming (4) with a kit from Boehringer-Mannheim Biochemical Corp. (Indianapolis, Ind.). DNA sequencing was done on double-stranded templates (7) by the method of Sanger et al. (13) using a Sequenase 2.0 kit (U.S. Biochemical Corp., Cleveland, Ohio).

DNA sequence resulting from unambiguous reading of both strands was compiled using the Staden alignment programs (16). Computer analyses of DNA and protein sequences were performed using the GCG programs (3). Database similarity searches were performed via e-mail to the National Center for Biotechnology Information using the BLASTX algorithm (1,5).

PCR amplification and cloning of *H. pylori* recA.

Degenerate PCR primers were designed based on conserved amino acid sequences of bacterial recA genes (11) and were synthesized at the Vanderbilt University DNA Diabetes Core Facility in a Milligen 7500 DNA synthesizer. Primer Rec1F was based on the amino acid sequence EIYGPE (SEQ ID NO:3) and had the sequence 5' GARATHTWYGGNCCNGA 3' (SEQ ID NO:4). Primer Rec2R was based on the reverse complement of the amino acid sequence NALKFYA (SEQ ID NO:5) and had the sequence 5' GCRTARAAYTTNARNGC 3' (SEQ ID NO:6). Thermocycler parameters were as follows: 1 minute at 94° C. (denaturation); 2 minute ramp to 37° C., followed by 2 min. at 37° C. (primer annealing); 2 minute ramp to 60° C., followed by 2 min. at 60° C. (extension).

Degenerate PCR on *H. pylori* 84-183 chromosomal DNA using these primers resulted in the amplification of 4 products, ranging in size from 350 bp to 800 bp. One of these was approximately the expected size (~470 bp), co-migrated with the product amplified from *E. coli* DH5α MCR, and was subsequently subcloned into the pT7Blue T-vector (Novagen, Madison, Wis.). A BLAST search of GenBank with the sequence of the subcloned PCR product verified that it was a portion of the *H. pylori* recA gene.

λZAPII was purchased from Stratagene (LaJolla, Calif.) and was used, according to the manufacture's instructions, to prepare a genomic library from *H. pylori* 84-183. Chromosomal DNA from 84-183 was partially digested with AluI. Digested DNA in the size range of 2–7 kb was purified and ligated with EcoRI linkers. The resulting fragments were ligated with EcoRI-digested, alkaline phosphatase-treated λZAPII arms and packaged into bacteriophage λ heads with Gigapack extracts (Stratagene).

To isolate the recA gene, a λZAPII library previously constructed from partially AluI-digested *H. pylori* 84-183 chromosomal DNA was screened. The PCR-amplified recA fragment was used as probe and identified three plaques containing recA sequences. Each was excised to a pBluescript plasmid (Stratagene) by the addition of helper phage. Restriction analysis of these clones revealed that all contained identical 2.3 kb inserts. One of these was designated pSAT101 and was subjected to DNA sequence analysis (SEQ ID NO:1). One end of the insert was within an 820 bp open reading frame (ORF). The deduced amino acid sequence of this ORF showed high similarity to bacterial RecA proteins when used in a BLAST search of GenBank. Features of *H. pylori* recA sequence.

The partial DNA and protein sequences reported in SEQ ID NO:1 and SEQ ID NO:2, respectively, have many features typical of bacterial recA sequences. Consensus -35 and -10 promoter elements begin at positions 263 (TTGTGA) and 287 (TATAAT), respectively. The first ATG initiation codon of the following ORF is preceded by a ribosome binding site (RBS) located at position 339 (AGG). The ORF contained on pSAT101 is 273 codons in length and does not contain a termination codon. This ORF, therefore, is approximately 80% the length of a typical bacterial recA gene (352 codons for *E. coli* recA). Story et al. (17) identified amino acid residues that are highly conserved or invariant in bacterial RecA proteins and related bacteriophage and yeast recombination proteins. All of these residues were present and in the predicted location in the deduced amino acid sequence of the pSAT101 ORF (SEQ ID NO:2). The residues identified are glycine$^{67}$, lysine$^{73}$, threonine$^{74}$, aspartic acid$^{95}$, glutamic acid$^{97}$, tyrosine$^{104}$, aspartic acid$^{145}$, serine$^{146}$, asparigine$^{194}$, glutamine$^{195}$, and glycine$^{213}$.

Mutagenesis of cloned *H. pylori* recA gene.

To confirm that this gene was in fact *H. pylori* recA, isogenic mutants were constructed in which the recA coding sequence had been interrupted by antibiotic resistance markers. Fragments containing the kanamycin- and chloramphenicol-resistance genes were prepared as follows. The chloramphenicol marker from pRY109 (18) was subcloned into the PstI site of pBluescript to create pBS103, then isolated following HincII and SmaI digestion. The recA-containing plasmid pSAT101 was linearized at a unique Sty I site, located within codon 31 of the recA ORF. Following fill-in of these ends by Klenow enzyme, this molecule was ligated to either the kanamycin- or chloramphenicol-resistance fragments. After transformation into *E. coli* DH5αMCR and selection on appropriate antibiotics (carbenicillin and kanamycin, or carbenicillin and chloramphenicol), one colony was chosen from each ligation (pSAT101::kan and pSAT101::chlor).

Electropotation of *H. pylori* 84-183.

The plasmids pSAT101::kan and pSAT101::chlor were used as donor DNAs in electroporation of *H. pylori* 84-183. *H. pylori* 84-183 cells were scraped from 4 blood agar plates (24 hours old) and washed as described previously (15); this provided the cells for use in five electroporations. Approximately 1 μg of supercoiled donor plasmid was mixed with the washed cells and placed in a Gene-Pulser (Bio-Rad, Melville, N.Y.) and electroporated at 2500 V, 200Ω, and 25 μF (15). Cells were then plated onto blood agar plates without antibiotics. Following overnight growth at 37° C., the entire plate was swabbed and streaked onto blood agar plates containing either kanamycin or chloramphenicol (see above). Antibiotic-resistant colonies were harvested after 3 days growth at 37° C.

Following electroporation and plating on selective medium, 10 kanamycin-resistant colonies and one chloramphenicol-resistant colony were recovered. One kanamycin-resistant colony (93-226) and one chloramphenicol-resistant colony (93-227) were characterized further by Southern hybridization with probes for the recA gene, kanamycin- or chloramphenicol-resistance markers, and the pBluescript vector. As expected, insertion of the kanamycin-resistance marker in strain 93-226 caused a 1.4 kb increase in the size of the recA-containing SacI restriction fragment. Similarly, insertion of the chloramphenicol-resistance marker caused a 1.1 kb increase in the recA– containing SspI fragment of strain 93-227. In neither strain was the insertion of the antibiotic-resistance marker accompanied by insertion of vector sequences.

UV sensitivity of recA⁻ H. pylori.

To test for loss of activity of the H. pylori recA protein, the sensitivities of wild-type and recA⁻ strains to irradiation with ultraviolet light were assayed. Approximately 100 and 1000 CFU of bacteria were plated onto blood agar plates, which were then exposed to 254 nm UV light for varying amounts of time (FIG. 1). RecA+ and RecA– E. coli strains were used as controls in this experiment, as was an H. pylori 84-183 derivative in which a kanamycin-resistance marker had been inserted into the cagA locus. Survival of RecA+ E. coli remained high throughout the UV exposures of this experiment, while RecA– E. coli were killed rapidly. RecA+ H. pylori strains 84-183 and 93-225 were similar in their susceptibilities to UV, verifying that kanamycin-resistance per se had no effect on survival. Both RecA+ H. pylori strains were somewhat more sensitive to killing by UV than RecA+ E. coli. Survival of both RecA⁻ mutant strains 93-226 and 93-227 was similar to that seen for RecA– E. coli. Therefore, both 93-226 and 93-227 have phenotypes consistent with loss of RecA function.

Increased sensitivity of recA mutant to low pH.

Urease-expressing H. pylori strains are quite resistant to acidic pH when provided with physiological concentrations of urea. To test whether mutation of the recA gene affected the ability of H. pylori to survive incubation in low pH, the assay of Perez-Perez et al. (10) was used. Phosphate buffers of different pH were prepared as follows. The pH of 0.2M dibasic sodium phosphate was adjusted to 7.0 with 0.2M monobasic sodium phosphate, or adjusted to 4.0 or 3.3 with 0.1M citric acid. Suspensions of the wild-type strain 84-183 and its isogenic recA mutant 93-226 were incubated in parallel conditions of pH 7.0, pH 4.0, and pH 3.3, either in the presence or absence of 10 mM urea. Following 1 hour incubation at 37° C., the cells were diluted in phosphate buffer (pH 7.0) and rapidly spread on blood agar plates. The number of surviving colonies was counted following five days growth on plates. The kill was determined as the log of the number of bacteria killed at pH 4.0 or 3.3 as compared to that occurring at pH 7.0.

The average of the results of two such experiments is shown in FIG. 2. In the presence of urea at pH 4.0, the kill was similar for both 84-183 and 93-226. However, in the presence of urea at pH 3.3, the recA strain was killed to a level about 13 times greater than that of the wild-type strain. A similar result was seen in the absence of urea at pH 4.0, where 93-226 was killed to a level about 24 times greater than that of 84-183. Almost complete killing of both strains was observed at pH 3.3 in the absence of urea, and an accurate calculation of the difference in survival between strains was not possible. These results indicate that the recA gene product plays a role in the survival of H. pylori at low pH.

Generation of recA⁻vacA⁻ mutant.

The Donnenberg reference provides a general method of creating mutations that can be used for construction of double or triple mutants such as recAcagA, recAvacA, or recAcagAvacA. For example, a deletion in cagAor vacA would be made as described by Donnenberg and Kaper, and then a cagA or vacA mutant strain made by introducing the mutated gene into H. pylori. A mutated recA gene (constructed either as described herein, or as by Donnenberg) would then be introduced into the cagA or vacA mutant strain by electroporation. The recA mutation should be the last one introduced into a strain, because the recA gene product is expected to be necessary for the recombination needed to integrate the mutated sequences into the H. pylori chromosome.

A 1.6 kb fragment encoding the first 1236 bp of the vacA ORF plus 393 bp of upstream sequence was PCR-amplified from H. pylori 60190 DNA, and subcloned in pT7Blue to create pCTB8. This plasmid was partially digested with EcoRI, and ligated with a C. coli kanamycin (km) resistance gene (22,23). Plasmid pILL 600 was used as a source of a Campylobacter coli kanamycin (km) resistance gene (22, 23). More specifically, pCTB8 was PCR-amplified from H. pylori 60190 DNA, using primers [(5' GTGAAAGC-GAAAAACAAG 3') (SEQ ID NO:7) and (5' AAGAGAAGCTTTAAACCCTCC 3') (SEQ ID NO:8)]. The km cassette from pILL600 (22,23) was ligated into the unique EcoRI site of pCTB8 to create pCTB8:km.

EXAMPLE 2

Strains and growth conditions.

Strains and plasmids used in this study are listed in Table 1. Conditions are as described in Example 1.

DNA techniques.

DNA techniques are as described in Example 1.

PCR amplification and cloning of H. pylori recA.

A degenerate PCR product was obtained and was subcloned into the pT7Blue(R) T-vector from Novagen (Madison, Wis.) by ligating vector and insert at a molar ratio of 3:1 (vector:insert) as described in Example 1. λZAPII (Stratagene, LaJolla, Calif.) was used to prepare two genomic libraries from H. pylori 84-183. The first library is described in Example 1.

The second library was constructed from chromosomal DNA digested to completion with HindIII, end-repaired by Klenow enzyme, and ligated with EcoRI linkers. Both types of fragments were ligated separately with EcoRI-digested, alkaline phosphatase-treated λZAPII arms and packaged into bacteriophage 1 heads with packaging extracts (Stratagene or Promega). Following identification of the desired λ clones by hybridization with the PCR-amplified fragment of H. pylori recA, plaques were purified and recombinant pBluescript plasmids were recovered following addition of R408 helper phage.

To isolate the entire recA gene, a λZAPII library previously constructed from partially AluI-digested H. pylori 84-183 chromosomal DNA was screened. As described in Example 1 for obtaining a 5' portion of the gene, the PCR-amplified recA fragment was used as probe and identified three plaques containing recA sequences. Each recombinant was excised to a pBluescript plasmid by the addition of helper phage. Restriction analysis of these clones revealed that all contained identical 2.3 kb inserts. One of these was designated pSAT101 (see Example 1 and FIG. 3) and was subjected to DNA sequence analysis. One end of the insert was within an 820 bp open reading frame (ORF), whose predicted amino acid sequence showed high similarity to bacterial RecA proteins when used in a BLAST search of GenBank (see Example 1).

Figure 3:
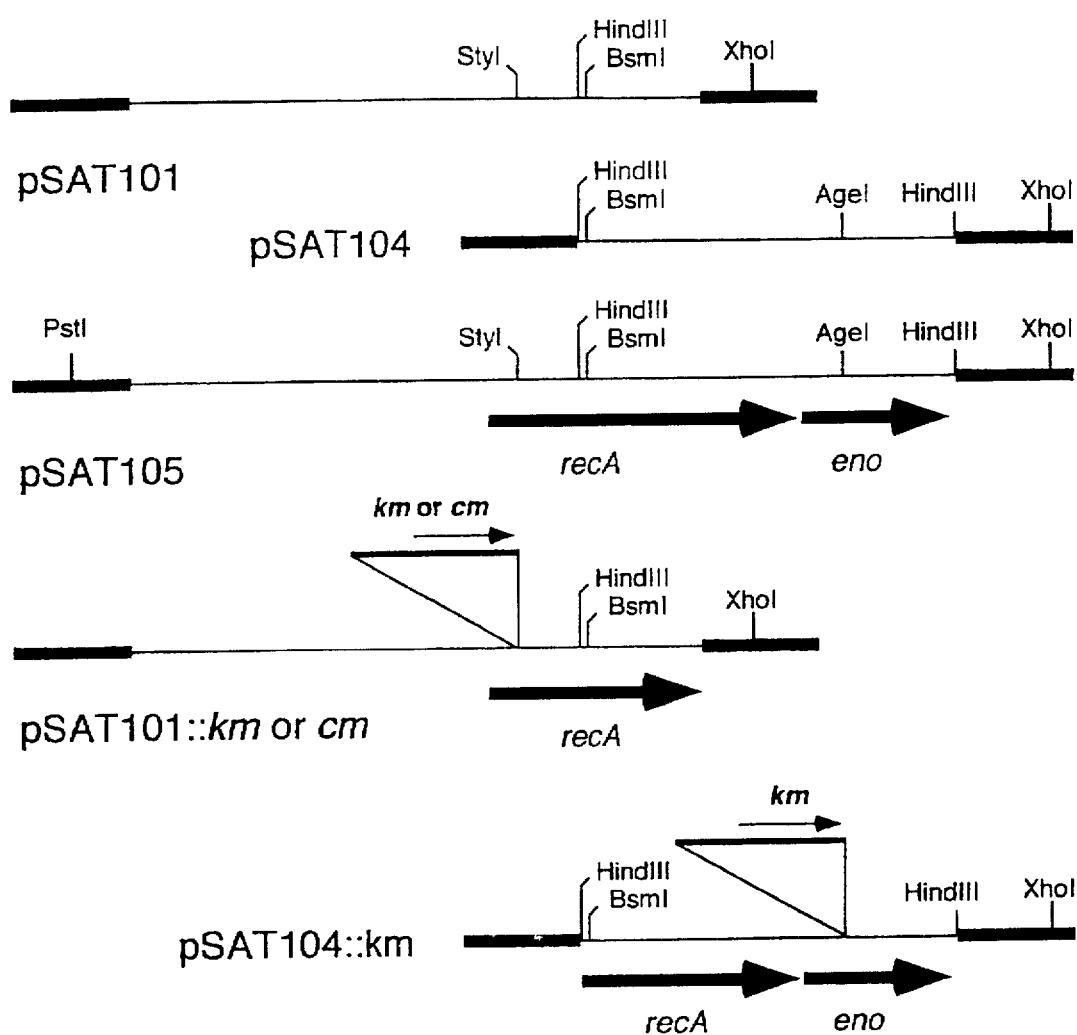
FIG. 3 shows the isolated clones used to obtain the present nucleic acids.

Since the 3' end of this ORF was not contained on pSAT101, a library of 84-183 DNA digested to completion with HindIII was constructed. Using the recA PCR probe a clone which contained the desired 1.4 kb HindIII fragment was identified. The resulting excised plasmid (pSAT104) was found to contain the 3' end of the recA gene, as well as a portion of an ORF immediately downstream (FIG. 3). The intact recA gene was reconstructed from pSAT101 and pSAT104 as follows. A 3.8 kb BsmI+XhoI fragment of pSAT101 containing the vector and the 5' end of recA was ligated with the 1.4 kb BsmI+XhoI fragment of pSAT104 (containing the 3' end of recA). The desired plasmid (pSAT105) was isolated following transformation of *E. coli* DH5αMCR (FIG. 3). The DNA sequences of the ligation junctions were determined to verify correct assembly.

A search of GenBank identified high similarity of the protein predicted by the downstream partial ORF to enolase proteins (Eno) of bacteria, yeasts, and mammals. Similarities to bacterial enolases was approximately 73–74% (*Bacillus subtilis* and *Zymomonas mobilis*). The location of the eno gene immediately downstream from recA was similar to the arrangement at the recA locus in *Campylobacter jejuni* (27).

Features of *H. pylori* recA/eno sequences.

The adjoined DNA sequences of pSAT101 and pSAT104 (SEQ ID NO:9) identify the presence of two genes. The 1044 bp recA ORF begins with the ATG at position 350, and is preceded by a putative (AGGT) ribosome binding site (RBS) located at position 340. The recA gene terminated at position 1393 with a TAA codon. Immediately following the recA termination codon was the probable RBS (AGGA) for the eno gene at position 1396. The ATG codon at position 1405 initiated a 533 bp ORF (eno) which continued to the end of the DNA cloned in pSAT104. The only consensus promoter elements in this region were −35 and −10 sites preceding the repreceding the recA ORF, at positions 264 (TTGTGA) and 288 (TATAAT), respectively. No transcriptional terminator was present between the recA and eno genes, although an 11 bp inverted repeat resembling a terminator (DG=−7.5 kcal/mol) was found within the eno gene at positions 1570 to 1598 (SEQ ID NO:9). The protein predicted by the recA ORF was 347 amino acids in length with a molecular mass of 37.6 kDa. Due to the high degree of amino acid conservation between bacterial RecA proteins (11), the predicted protein sequence of *H. pylori* RecA shared several features with 44 known RecA sequences. The amino acid residues that are highly conserved or invariant in bacterial RecA proteins and related bacteriophage and yeast recombination proteins identified by Story et al. (17) were all present and in the predicted location in the deduced amino acid sequence of the recA ORF (SEQ ID NO:9). The residues identified were glycine[67], lysine[73], threonine[74], aspartic acid[95], glutamic acid[97], tyrosine[104], aspartic acid[145], serine[146], asparagine[194], glutamine[195], and loci are known to be involved in ATP binding, DNA interactions, or stabilization of RecA protein structure (17). Overall homology of *H. pylori* RecA to other bacterial RecA proteins was between 75% (*C. jejuni*) and 54% (*Acidiphilium facilis*) amino acid identity.

Mutagenesis of cloned *H. pylori* recA and eno genes.

recA⁻ mutants were generated as described in Example 1. To mutagenize the eno gene, pSAT104 was linearized at the unique AgeI site in codon 44 of the eno gene. The ends of this fragment were made blunt using Klenow enzyme and ligated with the blunt-ended km-resistance fragment as above. A plasmid was isolated that contained the desired insertion and was designated pSAT104::km. The mutated eno gene was returned to the 84-183 chromosome by natural transformation, resulting in strain 94-49. Proper replacement of the wild-type eno allele with the km-mutagenized allele was verified by PCR, and was not accompanied by insertion of vector sequences.

The orientations of km- and cm-fragment insertions in each of the above constructs were determined by DNA sequencing.

Electropotation and natural transformation of *H. pylori* 84-183.

For electroporation, *H. pylori* 84-183 cells were scraped from 24 hour cultures on four BAP and washed as described previously (15). Approximately 1 mg of supercoiled donor plasmid was mixed with the washed cells and placed in a Gene-Pulser (Bio-Rad, Melville. N.Y.) and electroporated at 2500 V, 200 W, and 25 mF (15). Cells then were inoculated onto BAP without antibiotics. Following overnight growth at 37° C., the entire plate was swabbed and streaked onto BAP containing either kanamycin or chloramphenicol. Antibiotic-resistant colonies were harvested after 3 days growth at 37° C. Electroporations using either no donor DNA or the non-mutagenized pSAT101 served as negative controls. Natural transformation experiments were done essentially as previously described (28) by concentrating the cells from a 24 hour culture grown on one BAP into 50 ml of saline. Following application of 10 ml spots of concentrated cells to a BAP, 10 ml of saline containing pSAT104::km (1 mg) or saline alone (negative control) was added to the cells and incubated in a $CO_2$ incubator at 37° C. overnight. The following morning, the cells were streaked onto BAP containing kanamycin. Kanamycin-resistant colonies were recovered as above.

Following electroporation and plating on selective medium, 10 kanamycin-resistant colonies and one chloramphenicol-resistant colony were isolated. One kanamycin-resistant colony (93-226) and one chloramphenicol-resistant colony (93-227) were characterized further by Southern hybridization with probes for the recA, km, or cm genes, and the pBluescript vector. As expected, insertion of the km-resistance gene in strain 93-226 caused a 1.4 kb increase in the size of the 7.0 kb recA-containing SacI restriction fragment. Similarly, insertion of the cm-resistance gene caused a 1.1 kb increase in the 4.0 kb recA-containing SspI fragment of strain 93-227. Lack of hybridization to pBluescript demonstrated that in neither strain was the insertion of the antibiotic-resistance gene accompanied by insertion of vector sequences. Southern analysis of the remaining nine kanamycin-resistant strains showed that they were identical to 93-226.

Sensitivities of mutants to UV light and MMS.

Figure 4A:
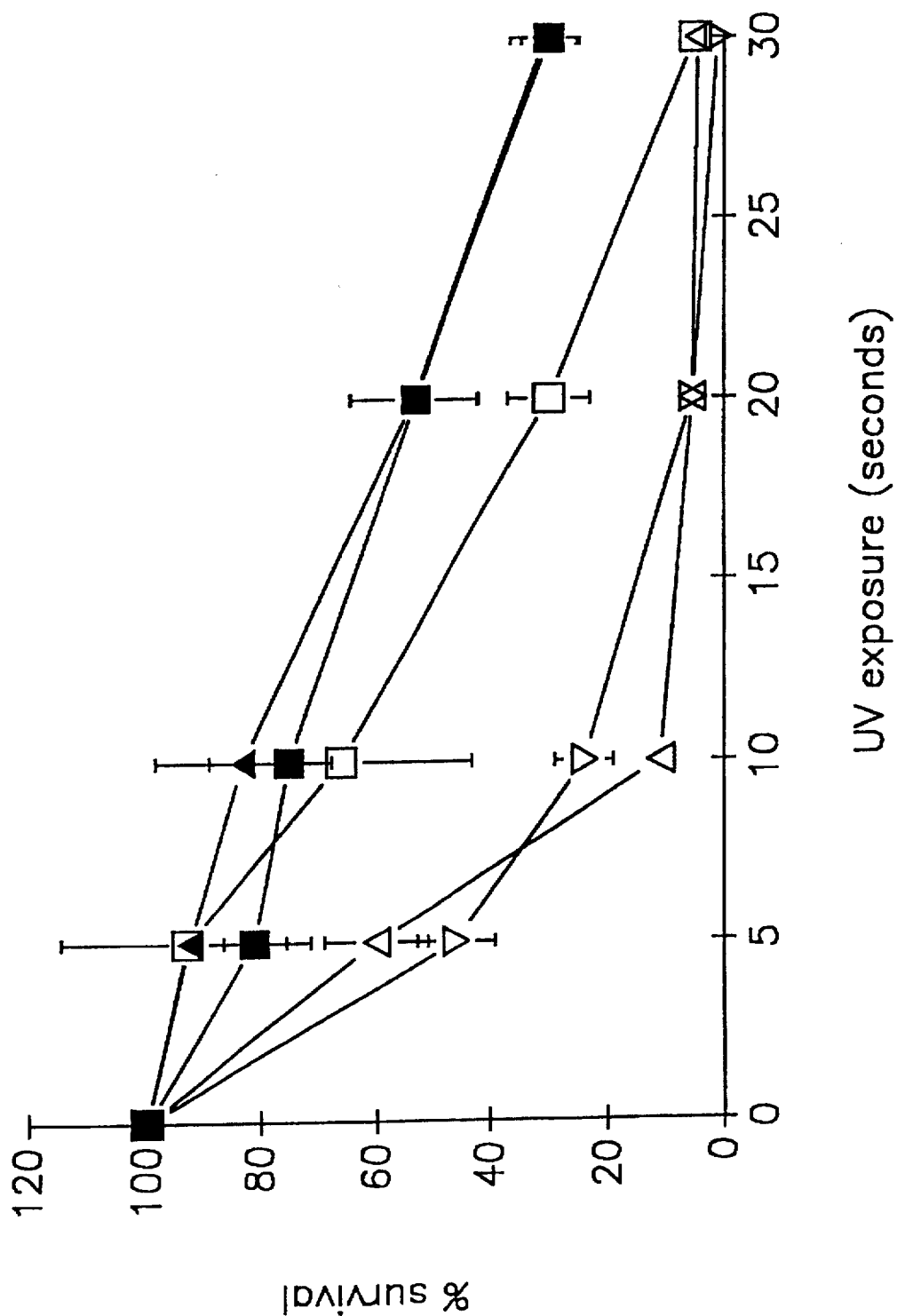
FIG. 4A shows the sensitivities of wild-type and mutant *H. pylori* to UV radiation determined by plotting the fractional survival of each strain versus exposure time or dose of DNA damaging agent. ● *E. coli* &1089 (recA⁺), ○ *E. coli* DH5αMCR (recA1), ▲ *H. pylori* 84-183 (recA⁺), ■ *H. pylori* 93-225 (recA⁺), △ *H. pylori* 93-226 (recA::km), ▽ *H. pylori* 93-227 (recA::cm), □ *H. pylori* 94-49 (eno::km).

To test for loss of activity of the *H. pylori* RecA protein, assays to determine the sensitivities of wild-type, recA, and eno strains to irradiation with 254 nm UV radiation or treatment with the DNA-damaging agent MMS (FIG. 4A and 4B) were performed as follows: 200–400 CFU of each strain (from 48 hour BAP cultures) were plated onto either BAP (UV experiments) or BAP containing various concentrations of MMS (Kodak Co., Rochester, N.Y.) in order to achieve a countable range of surviving colonies from a single plate. For UV experiments, the plates were dried briefly and exposed for varying amounts of time to 254 nm UV light generated by a Universal UV Lamp (Model 51402, Gelman-Camag) at a distance of 10.5 cm. The exposures were performed in a photographic dark room, and the plates were immediately wrapped in aluminum foil to prevent photoreactivation. Plates from both types of experiments were incubated for five days before the colonies were counted and the survival determined.

Figure 4B:
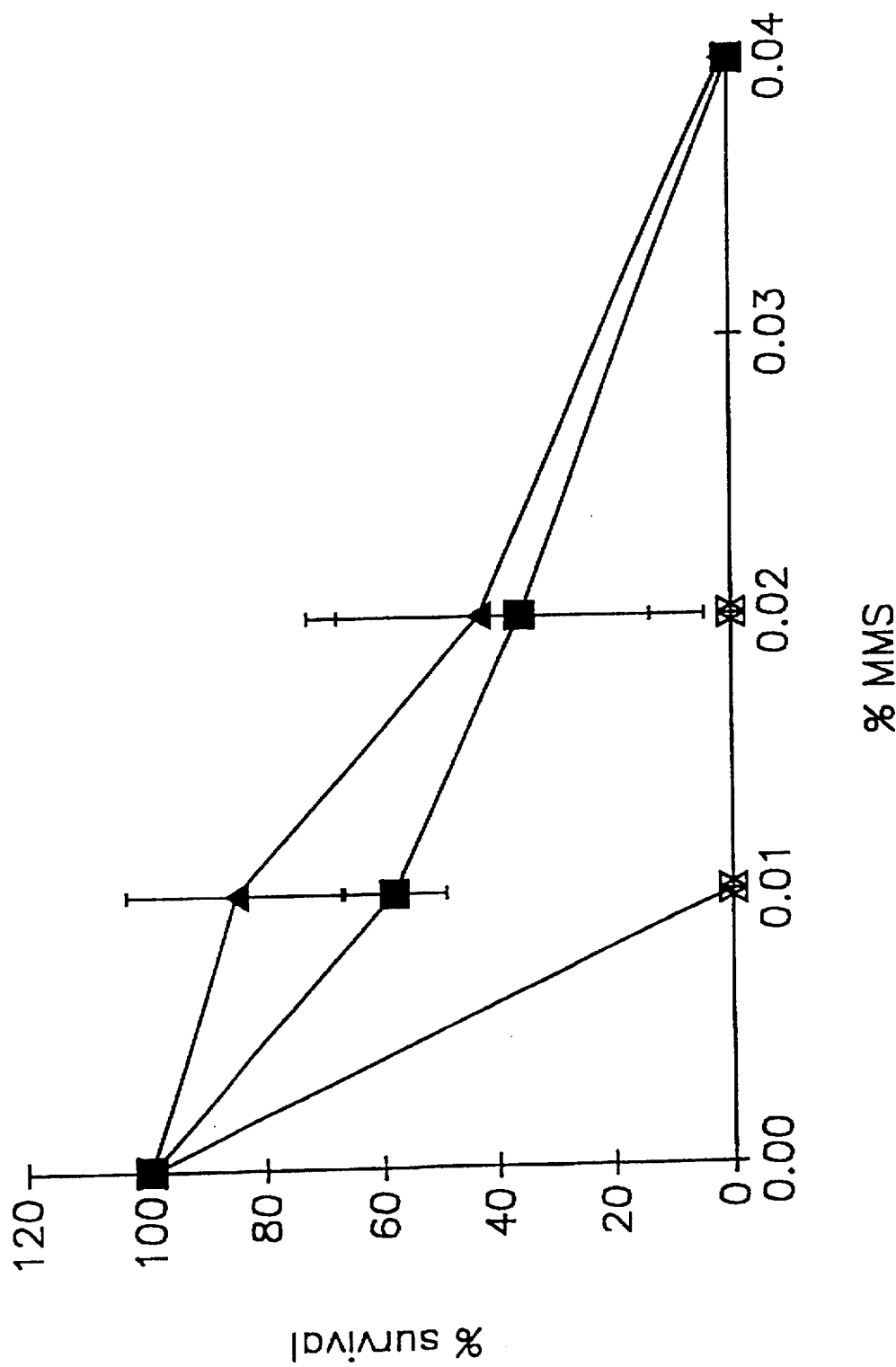
FIG. 4B shows the sensitivities of wild-type and mutant *H. pylori* to MMS determined by plotting the fractional survival of each strain versus exposure time or dose of DNA damaging agent.

E. coli strains Y1089 (recA$^+$) and DH5aMCR (recA1) were used as controls in this experiment, as was a recA$^+$ H. pylori 84-183 derivative (93-225) in which km had been inserted into the cagA locus (29). recA$^+$ H. pylori strains 84-183 and 93-225 were similar in their susceptibilities to UV, verifying that kanamycin-resistance per se had no effect on survival. Both recA$^+$ H. pylori strains were somewhat more sensitive to killing by UV than recA$^+$ E. coli. Survival of both recA mutant strains 93-226 and 93-227 was similar to that seen for recA E. coli. The eno mutant 94-49 showed UV sensitivity intermediate to those of wild-type and recA H. pylori. Parallel experiments were performed on recA mutants with exposure to MMS, with similar results (FIG. 4B). Both recA H. pylori strains showed greatly increased sensitivity to MMS relative to the two recA$^+$ H. pylori controls. Therefore, 93-226, 93-227, and to some extent 94-49, have phenotypes consistent with loss of RecA function.

Susceptibilities of recA and eno strains to antimicrobial agents.

Determinations (in triplicate) of the minimum inhibitory concentrations (MICs) for the antimicrobial agents ampicillin, ciprofloxacin, erythromycin, metronidazole, and tetracycline were achieved using the E-test (Remel Corp., Lenexa, Kans.), in which E-strips were placed onto BAP inoculated with 0.5 McFarland suspensions of 48 hour cultures of H. pylori strains. MICs were scored after 3 days growth.

As expected, the recA mutants were significantly more sensitive to metronidazole and ciprofloxacin, antimicrobials that cause DNA damage or interfere with replication (30, 31, 32). Interestingly, the recA strains also were significantly more sensitive to ampicillin, erythromycin, and tetracycline, that have different mechanisms of action. Strain 94-49 showed susceptibility to metronidazole (and to a lesser extent to ciprofloxacin) intermediate to those of the wild-type and recA mutants. Susceptibilities to the remaining antimicrobials was similar to those observed with the recA mutants. These results suggest that two different phenomena may be responsible for the relative sensitivities of the recA and eno mutants to these antimicrobials. Increased sensitivity of the eno mutant to metronidazole (and possibly ciprofloxacin) might result from decreased expression of recA in the eno mutant, while susceptibilities to the others may result from decreased expression of eno in both types of mutants.

Sensitivity of mutants to low pH.

Little is known about the exact environment in which H. pylori lives in the stomach. One condition that is certainly encountered is the low pH of gastric juice, and a role for the H. pylori urease protein in acid survival has been proposed (33, 34). Therefore, to test whether recA or eno mutations had an effect on survival at low pH, acid sensitivity experiments were performed on the wild-type strain 84-183 and the recA mutant, 93-226. Using the assay of McGowan et al. (35), approximately $1\times10^8$ CFU of the wild-type strain 84-183, the recA mutant 93-226, or the eno mutant 94-49 were incubated in phosphate buffer (pH 7.0, pH 4.0, or pH 3.3), either in the presence or absence of 10 mM urea. Following a 1 hour incubation at 37° C., the cells were diluted in phosphate buffer (pH 7.0) and rapidly spread on BAP. The number of surviving colonies was assayed following five days growth. The number ($\log_{10}$) of bacteria killed at pH 4.0 or 3.3 compared to that occurring at pH 7.0 was determined. Statistical significance was determined using a one-tailed Student's t-test.

In the presence of urea at pH 4.0, survival of 93-226 was similar to that of 84-183. However, at pH 3.3 in the presence of urea, 93-226 was nearly ten-fold more sensitive to acid killing than 84-183. A similar difference in survival was seen at pH 4.0 in the absence of urea, indicating that the acid-sensitive phenotype in 93-226 was not due to interference with urease function. Similar to what was observed in sensitivities to UV and metronidazole, the eno mutant 94-49 was killed by low pH to an extent intermediate between the wild-type strain and the recA mutant. The recA or eno strains did not survive incubation at pH 3.3 in the absence of urea, and therefore evaluation of survival relative to wild-type was not possible.

Reverse transcription-polymerase chain reaction (RT-PCR).

To investigate directly whether insertion of an antibiotic resistance cassette into recA had polar effects on eno expression, reverse transcription-PCR (RT-PCR) was performed on RNA samples prepared from wild-type (84-183), recA (93-226) and eno (94-49) H. pylori. RNA was prepared from 30 hour cultures of wild-type and mutant H. pylori grown on BAP as previously described (12). A 10 mg sample of each RNA was treated with RNase-free DNase (Promega) to remove contaminating DNA. Control PCR experiments verified that detectable DNA was removed by this treatment. Next cDNA from 1 mg aliquots of the DNase-treated RNA samples were prepared as previously described (36), using MMLV reverse transcriptase (Gibco-BRL, Gaithersburg, Md.) and random hexamer oligonucleotide primers (Pharmacia LKB Biotech, Piscataway, N.J.). The reaction mixtures were diluted to 20 ml with H$_2$O, and 1 ml of each was used as template for PCR (36) using oligonucleotide primers specific for various regions of the recA, eno, and km genes (Table 1). PCR products were analyzed by electrophoresis through 1.0% agarose.

A primer pair encompassing the 3' end of the recA gene and the 5' end of the eno gene amplified the expected product in these H. pylori strains, supporting the DNA sequence data that the recA and eno genes are co-transcribed. Significant transcription of recA occurred 3' of the point of insertion of the km cassette in recA mutant 93-226, and proceeded at least into the 5' end of the eno gene. However, the amount of transcript corresponding to the 3' end of the cloned portion of eno was greatly decreased in strain 93-226, suggesting that insertion of the km cassette into recA exerted polar effects on production of a full-length eno transcript. In contrast to that seen with km cassette insertion into recA, insertion of km into eno did not result in appreciable transcription of downstream eno sequences. Insertion of km into eno also did not grossly affect the amount of recA-specific transcript. Northern hybridization supported the RT-PCR data, and indicated that recA and eno are co-transcribed and that insertion of the km cassette into recA diminished the amount of eno-specific transcript.

The sequence shown in SEQ ID NO:9 has been deposited into GenBank under the accession number U13756.

Effect of recA mutation on genetic stability.

Lack of RecA function is expected to afford increased genetic stability to other markers that are necessary for a vigorous immune response. For example, the CagA immunodominant antigen undergoes size variation in vitro. If expression of a certain CagA size variant is important in achieving a protective immune response, mutation of recA should prevent variation to a different size. recA mutation is likely to greatly diminish the DNA transformation frequency of *H. pylori*. Most strains of *H. pylori* are naturally competent for DNA uptake (28), and DNA transformation may occur in vivo. The present *H. pylori* recA mutant (93-227) was completely deficient in ability to be transformed by a DNA fragment that contained a km cassette insertion into the cagA gene. Inhibition of transformation via recA mutation is desirable, preventing reversion of an attenuated strain to virulence through uptake of DNA from resident *H. pylori*. Similarly, recA mutation should prevent reversions based on homologous recombination involving endogenous sequences.

Animal model studies with a *H. pylori* recA$^-$ mutant.

To determine whether RecA function is critical for *H. pylori* to establish or maintain an infection, a euthymic mouse model for *H. pylori* infection was used according to the method of Karita et al. (39).

Six-wk-old male BALB/C euthymic nude mice and BALB/C euthymic mice were used (Nippon SLC, Hamamatsu-shi, Shizuoka-ken, Japan). Nude mice were maintained in laminar flow racks since birth, and euthymic mice were maintained in an ordinary environment. Food and drinking water for the nude mice were autoclaved before use, whereas those for the euthymic mice were not autoclaved.

Two-milliliter aliquots of the culture fluid of *H. pylori* with a concentration of $10^8$ organisms/ml (adjusted as described above) were prepared. Forty-eight-hour broth culture of *H. pylori* was used in the preparation of inocula. Cultures of *H. pylori* were grown in Brucella broth (BBL, Becton Dickinson and Co., Cockeysville, Md.) with 2% fetal bovine serum in shake flasks (120 rpm) at 37° C. under a gas mixture consisting of 80% $N_2$, 15% $CO_2$, and 5% $O_2$. Gas was replaced at 24 h. Then, $10^8$ to $10^9$ colony-forming units (CFU) of wild-type and recA *H. pylori* were administered orally to each of 8 6-wk-old euthymic mice after 1 day of fasting, with a flexible tube (18-guage) immediately after the *H. pylori* fluid was prepared. Two milliliters of Brucella broth supplemented with 2% fetal bovine serum were administered to the controls as control broth.

Mice were sacrificed at 1 week and 4 weeks post-inoculation (4 mice each) and their stomachs isolated and homogenized. Colonization was evidenced by culture of *H. pylori* from the gastric homogenates. In contrast to the wild-type *H. pylori* strain, recA$^-$ *H. pylori* were unable to colonize the stomachs of these animals. The mechanism(s) of the inability to recA$^-$ *H. pylori* to colonize euthymic mice is unknown, but could be due to several factors including their increased sensitivity to gastric acid or increased killing by immune cells present in the gastric epithelium.

Throughout this application various publications are referenced by numbers within parentheses. The disclosures of these publications in their entireties are hereby incorporated by reference into this application in order to more fully describe the state of the art to which this invention pertains. The full citations for these publications are as follows:

REFERENCES

1. Altschul, S. F., W. Gish, W. Miller, E. W. Myers, and D. J. Lipman. 1990. Basic local alignment search tool. J. Mol. Biol. 215:403–410.
2. Biswas, G. D., J. Graves, R. Schwalbe, and P. F. Sparling. 1986. Construction of isogenic gonococcal strains varying in the presence of a 4.2-kilobase cryptic plasmid. J. Bacteriol. 167:685–694.
3. Devereux, J., P. Haeberli, and O. Smithies. 1984. A comprehensive set of sequence analysis programs for the VAX. Nucleic Acids Res. 12:387–395.
4. Feinberg, A. P. and B. Vogelstein. 1983. A technique for radiolabeling DNA restriction endonuclease fragments to high specific activity. Anal. Biochem. 132:6.
5. Gish, W. and D. J. States. 1993. Identification of protein coding regions by database similarity search. Nature Genetics. 3:266–72.
6. Hanahan, D. 1983. Studies on transformation of *Escherichia coli* with plasmids. J. Mol. Biol. 166:557.
7. Kraft, R., J. Tardiff, K. S. Krauter, and L. A. Leinwand. 1988. Using mini-prep plasmid DNA for sequencing double stranded templates with Sequenase. Biotechniques. 6:544–546.
8. Labigne-Roussel, A., P. Courcoux, and L. Tompkins. 1988. Gene disruption and replacement as a feasible approach for mutagenesis of *Campylobacter jejuni*. J. Bacteriol. 170:1704–1708.
9. Perez-Perez, G. I. and M. J. Blaser. 1987. Conservation and diversity of *Campylobacter pyloridis* major antigens. Infect. Immun. 55:505–513.
10. Perez-Perez, G. I., A. Z. Olivares, T. L. Cover, and M. J. Blaser. 1992. Characteristics of *Helicobacter pylori* variants selected for urease deficiency. Infect. Immun. 60:3658–3663.
11. Roca, A. I. and M. M. Cox. 1990. The RecA protein: structure and function. [Review]. Crit Rev Biochem Mol Biol. 25:415–56.
12. Sambrook, J., E. F. Fritsch, and T. Maniatis. 1987. Molecular Cloning: A laboratory manual, pages. Second edition, ed.; Cold Spring Harbor Lab., Cold Spring Harbor, N.Y.
13. Sanger, F., S. Nicklen, and A. R. Coulson. 1977. DNA sequencing with chain terminating inhibitors. Proc. Natl. Acad. Sci. U.S.A. 74:5463–5467.
14. Schleif, R. F. and P. C. Wensink, 1981. Practical methods in molecular biology. 98–105. In: Springer Verlag, N.Y.
15. Segal, E. D. and L. S. Tompkins. 1993. Transformation of *Helicobacter pylori* by electroporation. BioTechniques. 14:225–226.
16. Staden, R. 1982. Automation of the computer handling of gel reading data produced by the shotgun method of DNA sequencing. Nucleic Acids Res. 10:4731–4751.
17. Story, R. M., D. K. Bishop, N. Kleckner, and T. A. Steitz. 1993. Structural relationship of bacterial RecA proteins to recombination proteins from bacteriophage T4 and yeast. Science. 259:1892–1896.
18. Yao, R., R. A. Alm, T. J. Trust, and P. Guerry. 1993. Construction of new Campylobacter cloning vectors and a new mutational cat cassette. Gene.
19. Young, R. A. and R. W. Davis. 1983. Efficient isolation of genes by using antibody probes. Proc. Natl. Acad. Sci. U.S.A. 80:1194–1198.
20. Cover, T. L., and Blaser, M. J. (1992) Annu. Rev. Med. 43, 135–145.
21. Correa, P. (1992) Cancer Res. 52, 6735–6740.
22. Hentschel, E., Brandstatter, G., Dragosics, B., Hirschl, A. M., Nemec, H., Schutze, K., Taufer, M., and Wurzer, H. (1993) N. Engl. J. Med. 328, 308–312.
23. McKnight, S. L. and R. Kingsbury (1982) Transcriptional control signals of a eukaryotic protein-coding gene. Science 217:316.

24. Kunkel, T. A. (1985) Rapid and efficient site-specific mutagenesis without phenotypic selection. Proc. Natl. Acad. Sci. 82:488.
25. Eaton, J. A., C. L. Brooks, D. R. Morgan, and S. Krawowka (1991). Essential role of urease in pathogenesis of gastritis induced by *Helicobacter pylori* in gnotobiotic piglets. Infect. Immun. 59:2470-5.
26. Eaton, K. A., D. R. Morgan and S. Krakowka (1992) Motility as a factor in the colonisation of gnotobiotic piglets by *Helicobacter pylori*. J. Med. Microbiol. 37:123-7.
27. Guerry, P., P. M. Pope, D. H. Burr, J. Leifer, S. W. Joseph, and A. L. Bourgeois. 1994. Development and characterization of recA mutants of *Campylobacter jejuni* for inclusion in attenuated vaccines. Infect. Immun. 62:426-432.
28. Wang, Y., K. P. Roos, and D. E. Taylor. 1993. Transformation of *Helicobacter pylori* by chromosomal metronidazole resistance and by a plasmid with a selectable chloramphenicol resistance marker. J. Gen. Microbiol. 139:2485-2493.
29. Thompson, S. A. Unpublished data.
30. Knight, R. C., I. M. Skolimowski, and D. I. Edwards. 1978. The interaction of reduced metronidazole with DNA. Biochem. Pharmacol. 27:2089-2093.
31. Sioud, M., and P. Forterre. 1989. Ciprofloxacin and etoposide (VP16) produce a similar pattern of DNA cleavage in a plasmid of an archaebacterium. Biochemistry. 28:3638-3641.
32. Wolfson, J. S., and D. C. Hooper. 1985. The fluoroquinolones: structures, mechanisms of action and resistance, and spectra of activity in vitro. Antimicrob. Agents Chemother. 28:581-586.
33. Labigne, A., V. Cussac, and P. Courcoux. 1991. Shuttle cloning and nucleotide sequences of *Helicobacter pylori* genes responsible for urease activity. J. Bacteriol. 173:1920-1931.
34. Lee, A., J. Fox, and S. Hazell. 1993. Pathogenicity of *Helicobacter pylori*: a perspective. Infect. Immun. 61:1601-1610.
35. McGowan, C. C., T. L. Cover, and M. J. Blaser. 1994. The proton pump inhibitor, omeprazole, inhibits acid survival of *Helicobacter pylori* by a urease-independent mechanism. Gastroenterology. 107:1573-1578.
36. Peek, R. M., G. G. Miller, and M. J. Blaser. In press. Reverse transcription-polymerase chain reaction (RT-PCR) for bacterial and host gene expression in human gastric mucosa. In F. Megraud, N. Lee, and A. Lee (ed.), *Helicobacter pylori* techniques for clinical diagnosis and basic research. W. B. Saunders, Ltd.
37. Marchetti, M., Arico, B., Burroni, D., Figura, N., Rappuoli, and R., Ghiara P. 1995. Development of a Mouse Model of *Helicobacter pylori* infection that mimics uman disease. Science. 107:1573-1578.
38. Tompkins, Lucy S. and Stanley Falkow. 1995. The New Path to Preventing Ulcers. Science. 267:1821-1822.
39. Karita, M., Takashi, K., Kiwamu, O. and Nakazawa, T. New Small Animal Model for Human Gastric *Helicobacter pylori* Infection:Success in Both Nude and Euthymic Mice. 1991. Amer. J. of Gastroenterol. 86(11) :1596-1603.

---

What is claimed is:

1. An isolated nucleic acid encoding a *Helicobacter pylori* enolase.

2. The nucleic acid of claim 1 in a vector suitable for expressing the nucleic acid.

3. The nucleic acid of claim 2 in a host cell suitable for expressing the nucleic acid encoding the enolase.

4. The nucleic acid of claim 1, wherein the nucleic acid encodes amino acids 1 through 177 of the amino acid sequence defined in the Sequence Listing as SEQ ID NO:11.

5. The nucleic acid of claim 1, comprising a mutation that results in a non-functional enolase.

6. An isolated nucleic acid of at least 35 nucleotides that hybridizes with the nucleic acid of claim 4 under stringent conditions and has at least 85% complementarity with the segment of the nucleic acid to which it hybridizes, wherein the hybridizing nucleic acid encodes a *Helicobacter pylori* enolase or a portion thereof.

7. The nucleic acid of claim 6 in a vector suitable for expressing the nucleic acid.

8. The nucleic acid of claim 7 in a host cell suitable for expressing the nucleic acid encoding the enolase.

* * * * *